US012607633B2

(12) United States Patent
Legler et al.

(10) Patent No.: US 12,607,633 B2
(45) Date of Patent: Apr. 21, 2026

(54) METHODS AND COMPOSITIONS FOR THE DETECTION OF HOST PROTEIN CLEAVAGE BY GROUP IV VIRAL PROTEASES

(71) Applicant: The Government of the United States of America, as represented by the Secretary of the Navy, Arlington, VA (US)

(72) Inventors: Patricia M. Legler, Derwood, MD (US); Elaine Morazzani, Leesburg, VA (US); Pamela Glass, Frederick, MD (US)

(73) Assignee: The Government of the United States of America, as represented by the Secretary of the Navy, Arlington, VA (US)

( * ) Notice: Subject to any disclaimer, the term of this patent is extended or adjusted under 35 U.S.C. 154(b) by 1212 days.

(21) Appl. No.: 17/458,812

(22) Filed: Aug. 27, 2021

(65) Prior Publication Data

US 2021/0389324 A1      Dec. 16, 2021

Related U.S. Application Data

(60) Continuation-in-part of application No. 16/413,282, filed on May 15, 2019, now abandoned, which is a
(Continued)

(51) Int. Cl.
*C12N 15/00*          (2006.01)
*C12N 7/00*          (2006.01)
(Continued)

(52) U.S. Cl.
CPC ......... *G01N 33/56983* (2013.01); *C12N 7/00* (2013.01); *C12N 9/22* (2013.01);
(Continued)

(58) Field of Classification Search
None
See application file for complete search history.

(56) References Cited

U.S. PATENT DOCUMENTS 8,137,924 B2      3/2012   Chapman et al.
2012/0202754 A1      8/2012   Schmidt et al.

FOREIGN PATENT DOCUMENTS

CA            2363088 A1 *   8/2000   .............. A61P 31/18

OTHER PUBLICATIONS

Campos-Gomez et al., "A novel cell-based assay to measure activity of Venezuelan equine encephalitis virus nsP2 protease," Virology 496: 77-89 (Year: 2016).*
(Continued)

*Primary Examiner* — M Franco G Salvoza
(74) *Attorney, Agent, or Firm* — US Naval Research Laboratory; Fariborz Moazzam

(57)              ABSTRACT
Proteases of Group IV (+)ssRNA viruses were found to act on a human sequences in addition to the viral sequences. The identity of the cleavable human sequences is disclosed. Detection of these sequences can act as a diagnostic of infection. It is contemplated that these findings could be employed to facilitate post-translational silencing at the level of protein (e.g., removal of existing proteins), thus serving as a protein analog to CRISPR/Cas9 and RNAi/RISC, and further to enable sequence-specific silencing of host functions without the modification of the host genome.

2 Claims, 19 Drawing Sheets

Specification includes a Sequence Listing.

nsP12                                    nsP23      nsP34

| nsP1 | nsP2 | HELICASE | PROTEASE | SAM MTase | nsP3 | nsP4 |

Related U.S. Application Data division of application No. 15/820,969, filed on Nov. 22, 2017, now abandoned.

(60) Provisional application No. 62/426,352, filed on Nov. 25, 2016.

(51) Int. Cl.

| | |
|---|---|
| *C12N 9/22* | (2006.01) |
| *C12N 9/96* | (2006.01) |
| *C12N 15/11* | (2006.01) |
| *C12N 15/90* | (2006.01) |
| *C12Q 1/37* | (2006.01) |
| *G01N 33/569* | (2006.01) |

(52) U.S. Cl.

CPC ................ *C12N 9/96* (2013.01); *C12N 15/11* (2013.01); *C12N 15/902* (2013.01); *C12Q 1/37* (2013.01); *C12N 2310/20* (2017.05); *C12N 2770/36111* (2013.01); *C12N 2770/36131* (2013.01); *G01N 2333/181* (2013.01); *Y02A 50/30* (2018.01)

(56) References Cited

OTHER PUBLICATIONS

"The SARS-CoV-2 SSHHPS Recognized by the Papain-like Protease" ACS Infect. Dis. 2021, 7, 6, 1483-1502.

Hu, X., Compton, J. R., Legler, P. M. Analysis of Group IV Viral SSHHPS Using In Vitro and In Silico Methods. J. Vis. Exp. (154), e60421, doi:10.3791/60421 (2019).

Biochemistry. May 31, 2016; 55(21): 3007-3019. doi:10.1021/acs.biochem.5b00992.

Morazzani EM, Compton JR, Leary DH, Berry AV, Hu X, Marugan JJ, Glass PJ, Legler PM. Proteolytic cleavage of host proteins by the Group IV viral proteases of Venezuelan equine encephalitis virus and Zika virus. Antiviral Res. Apr. 2019;164:106-122. doi: 10.1016/j.antiviral.2019.02.001.

* cited by examiner

```
TRIM14 (human)    DCFATGRHYWEVDVQEAGA↓GWWVGA

VEEV nsP12        VEEPTLEADVDLMLQEAGA↓GSVETP
VEEV nsP23        LSSTLTNIYTGSRLHEAGC↓APSYHV
VEEV nsP34        TREEFEAFVAQQQRFDAGA↓YIFSSD

EEEV nsP12        VDKETVEADIDLIMQEAGA↓GSVETP
EEEV nsP23        LSVVLNNIYQGSTQHEAGR↓APAYRV
EEEV nsP34        AEFDEFVRRHSNXRYEAGA↓YIFSSE

WEEV nsP12        IEKETVEAEVDLIMQEAGA↓GSVETP
WEEV nsP23        LGVVLDNIYQGSTRYEAGR↓APAYRV
WEEV nsP34        AELDEYIRQHSNXRYEAGA↓YIFSSE

CHIKV nsP12       QEDVQVEIDVEQLEDRAGA↓GIIETP
CHIKV nsP23       VMNNQLNAAFVGQVTRAGC↓APSYRV
CHIKV nsP34       DWSTCSDTDDELRLDRAGG↓YIFSSD

SFV nsP12         AETGVVDVDVEELEYHAGA↓GVVETP
SFV nsP23         MNTKLSAVYAGEAMHTAGC↓APSYRV
SFV nsP34         SGITFGDFDDVLRLGRAGA↓YIFSSD

SINV nsP12        DAAAEVICEVEGLQADVGA↓ALVETP
SINV nsP23        HLNCVVSSVYEGLRDGVGA↓APAYRS
SINV nsP34        RRRRGQKKTEYXLTGVGG↓YIFSTD
```

FIG. 1C

| Lane | Inhibitor | Relative Band Intensity | Common Name | % Inhibition |
|---|---|---|---|---|
| 1 | Uncut | 1.00 | | |
| 2 | Cut | 0.11 | | |
| 3 | MLS001401425-01 | 0.15 | | |
| 4 | MLS000028372-01 | 0.90 | E-64d | 89% |
| 5 | MLS000759541-01 | 0.09 | | |
| 6 | MLS001217487-01 | 0.09 | | |
| 7 | MLS001163999-01 | 0.11 | | |
| 8 | MLS002699430-01 | 0.12 | | |
| 9 | 3,3-diaminobenzadine | 0.11 | | |

| Lane | |
|---|---|
| 1 | CHIKV nsP2 protease alone |
| M | Marker |
| 2 | SFV17 uncut |
| 3 | SFV17 with CHIKV nsP 2 |
| 4 | SFV25 uncut |
| 5 | SFV25 with CHIKV nsP 2 |
| 6 | VEEV P12 uncut |
| 7 | VEEV P12 with CHIKV nsP2 |
| 8 | VEEV P23 uncut |
| 9 | VEEV P23 with CHIKV nsP2 |
| 10 | VEEV P34 uncut |
| 11 | VEEV P34 with CHIKV nsP2 |

FIG. 2F

| PROTEIN | CALCULATED UNCUT MW (Da) | CALCULATED CUT MW (Da) |
|---|---|---|
| TRIM14-Nterm His-Tag | 51,098 | 38,442 |
| TRIM14 | 49,773 | 37,230 |
| TRIM14alpha | 45,112 | 37,230 |
| TRIM14beta | 28,347 | (NO CLEAVAGE SITE) |

METHODS AND COMPOSITIONS FOR THE DETECTION OF HOST PROTEIN CLEAVAGE BY GROUP IV VIRAL PROTEASES

CROSS-REFERENCE TO RELATED APPLICATIONS

This Application claims the benefit as a continuation-in-part of U.S. patent application Ser. No. 16/413,282 filed May 15, 2019, which is a division of U.S. patent application Ser. No. 15/820,969 filed on Nov. 22, 2017 with priority to U.S. Provisional Application 62/426,352 filed on Nov. 25, 2016, the entirety of each of which is incorporated herein by reference.

FEDERALLY-SPONSORED RESEARCH AND DEVELOPMENT

The United States Government has ownership rights in this invention. Licensing inquiries may be directed to Office of Technology Transfer, US Naval Research Laboratory, Code 1004, Washington, DC 20375, USA; +1.202.767.7230; techtran@nrl.navy.mil, referencing NC 105124-US4

STATEMENT REGARDING PRIOR DISCLOSURES BY THE INVENTOR(S)

A prior disclosure, *ACS Infect. Dis.* 2021, 7, 6, 1483-1502, published May 21, 2021, was made by one or more of the inventors with other named authors. Those other authors who are not named as inventors of this patent application were working under the direction and supervision of at least one of the inventors.

BACKGROUND

Proteases from bacteria have long been known to recognize specific human proteins and cleave them. Their human host protein substrate specificities have been exploited to develop these enzymes into therapeutic tools, e.g. Botulinum neurotoxin used in the BoTox™ (botulinum toxin) treatment. Viral proteases of (+)ssRNA (single-stranded RNA) viruses can also cleave human proteins specifically and in cells for transient post-translational silencing without alteration of the host genome (see ref. 94 and U.S. Pub. 2019/0293649). While immunoblots can be used with infected cell lysates to detect host protein cleavage, such methods are generally time consuming. The stability of the cut products in cultured cells is variable and cleavage may occur post or co-translationally as some of these viral proteases are anchored to the ER membrane, complicating the detection of host protein cleavage in cells and the identification of the scissle bond. Thus, improved methods to systematically predict the host targets of a Group IV viral protease using bioinformatics, test the sequences for cleavage in vitro, identify the scissile bond, and confirm cleavage of the protein in virus-infected cells are needed.

BRIEF SUMMARY

In one embodiment, a method of post-translational silencing includes causing a mammalian host cell to express a viral protease and allowing the protease to recognize and cleave a target protein sequence endogenous to the host, thereby causing transient loss of function of a target protein that comprises the target protein sequence. The expression can be induced by, for example, infection with a virus (optionally an attenuated virus), the introduction of a plasmid, etc. Suitable viral proteases exist in Group IV (+)ssRNA viruses and include those of Venezuelan equine encephalitis virus (VEEV), severe acute respiratory syndrome coronavirus 2 (SARS-CoV-2), Middle East respiratory syndrome-related coronavirus (MERS-CoV), and Zika virus (ZIKV), among others.

In a further embodiment, the host cell is within a living organism and said protease expression is caused by an infection of the organism with an attenuated virus encoding said protease.

In another embodiment, a method of identifying targets for post-translational silencing or drug discovery includes comparing, a viral protease cleavage site against a database of mammalian host proteins, thereby identifying in silico one or more potential host targets of the protease; and then assaying the one or more potential host targets in vitro to confirm actual targets of the protease. The database comprises a listing of proteases and the target sequences cleaved by each protease. Optionally, the host targets of multiple viral proteases can be compared simultaneously. The comparison can be made via reference to a graph and/or using computer hardware and software.

In another embodiment, the present invention provides a series of molecular constructs comprised of a donor fluorophore moiety and an acceptor fluorophore moiety capable of fluorescence resonance energy transfer (FRET) and a linker peptide sequence containing a viral or host (human) sequence that is cleavable by an identified Group IV viral protease. The linker peptides of each substrate is comprised of SEQ ID NOs: 2-24. The recombinant viral proteases which cleave these substrates are comprised of SEQ ID NOs: 25-29. In one aspect, the donor and acceptor fluorophores are variants of green fluorescent protein and the substrates are expressed and purified from *E. coli*. In further aspects, the substrates of SEQ ID NOs: 2-24 are provided without fluorophores attached thereto and instead their cleavage (indicative of viral protease activity) is detected by other means, such as immunohistochemistry (IHC), enzyme linked-immunosorbent assay (ELISA), SDS-PAGE (sodium dodecyl sulphate-polyacrylamide gel electrophoresis), mass spectrometry, and/or flow cytometry. In a still further aspect, the substrates are used in a method for screening small molecule inhibitors of the viral proteases for drug discovery.

In a still further embodiment, a method of treatment includes obtaining biological material from an individual suspected of being infected with a Group IV virus; assaying the biological material to detect the presence or absence of a cleavage product of a protease of the Group IV virus; and if the cleavage product is detected, then providing the individual with a treatment against the Group IV virus, wherein the assaying comprises performing immunohistochemistry (IHC), enzyme linked-immunosorbent assay (ELISA), mass spectrometry, and/or flow cytometry.

In yet another embodiment, a method of treatment that uses the Group IV viral proteases of VEEV, ZIKV, SARS-CoV-2, or MERS for targeted destruction of host proteins containing the sequences (SEQ IDs 7-15, 19-24). An additional aspect is the incorporation of the cleavable sequences (SEQ IDs 7-15 or 19-24) in a transgenic animal model.

BRIEF DESCRIPTION OF THE DRAWINGS

FIGS. 1A through 1C illustrate the organization of the alphaviral nonstructural polyprotein. The nsP2 cysteine protease cleaves the polyprotein to produce nsP1, nsP2, nsP3, and nsP4. As seen in FIG. 1A, the nonstructural protein 2 (nsP2) contains an N-terminal region, a helicase, a papain-like cysteine protease, and SAM methyltransferase (SAM MTase). FIG. 1B shows the crystal structure (PDB 5EZS) of the recombinant form of the VEEV nsP2 protease used in the in vitro assays [SEQ ID NO: 25] (30) inhibited with E64d (30). The protease and SAM MTase domains pack together and, as identified by the inventors, residues within the SAM MTase are involved in substrate binding and recognition. The peptide-like E64d inhibitor binds beneath the β-hairpin at the interface of these two domains. The structure of the pre-cleavage nsP23 complex (PDB 4GUA) shows the packing of the nsP3 domain (90). FIG. 1C illustrates a sequence alignment of the TRIM14 protein with the three alphaviral nsP cleavage sites used in the substrates. The human TRIM 14 and the New World alphaviruses (SEQ ID Nos: 2, 4, 5, and 6) share the QEAGA↓G (SEQ ID NO: 1) sequence.

FIGS. 2A through 2F show results of in vitro FRET (fluorescence resonance energy transfer) and SDS-PAGE (sodium dodecyl sulphate-polyacrylamide gel electrophoresis) assays demonstrating the cleavage of substrates by various viral proteases. FIG. 2A shows the results from measurement of the recombinant VEEV nsP2 cysteine protease steady state kinetic parameters for the CFP-TRIM14-YFP substrate (TRIM14 with cyan and yellow fluorescent protein) [SEQ ID NO: 4] by the recombinant VEEV nsP2 cysteine protease [SEQ ID NO: 25] as measured in a microplate spectrofluorometer at R.T. in 50 mM HEPES pH 7.0 for 30 min. The $K_m$ and $V_{max}$ were comparable to those measured using similar substrates containing the VEEV nsP12 or nsP34 cleavage sites [SEQ. ID NOs: 2 and 3]. FIG. 2B shows results after the recombinant VEEV, eastern equine encephalitis virus (EEEV), western equine encephalitis virus (WEEV), or chikungunya virus (CHIKV) nsP2 cysteine proteases (5 μM) were incubated with 50 μM CFP-TRIM14-YFP substrate for 24 h at R.T. in 50 mM HEPES pH 7.0, 150 mM NaCl. Only the recombinant VEEV nsP2 cysteine protease [SEQ ID NO: 25] was able to digest the TRIM14 substrate completely in vitro during this time period. The recombinant WEEV and EEEV protease constructs spanning the same residue range had low activity in vitro in comparison to their viral counterparts; these proteases differ in sequence when compared with the VEEV nsP2 protease and may require additional regions of the nsP for full activity in vitro. The CHIKV protease was not predicted to cleave the TRIM14 sequence and the recombinant CHIKV nsP2 protease [SEQ ID NO: 29] did not show evidence of significant cleavage of this substrate which is consistent with its substrate specificities. FIG. 2C shows the effects of site-directed mutagenesis on cleavage of CFP-YFP substrates containing the SFV nsP12 cleavage site, the VEEV nsP12, nsP23, nsP34 cleavage sites and the TRIM14 sequence by the recombinant VEEV nsP2 protease. Cleavage reactions were run in 1×PBS pH 7.4 and 5 mM DTT and were incubated for 19 h at R.T. using 30 μM substrate and 2.2 μM enzyme prior to electrophoretic analysis. FIG. 2D shows the use of the CFP-YFP substrate carrying the junctional sequence between nsP3 and nsP4 of VEEV [SEQ ID No: 3] with the recombinant VEEV nsP2 cysteine protease. The top panel of FIG. 2D shows the cleavage of the substrate at varying concentrations monitored in a microplate reader in a continuous assay. The bottom panel of FIG. 2D shows the $K_m$ and $V_{max}$ measured for the V34 substrate [SEQ ID No: 3] and recombinant VEEV nsP2 cysteine protease using the continuous assay above in the absence of inhibitors. FIG. 2E shows that the cleavage of the CFP/YFP substrates by the viral proteases can be confirmed by separation in SDS-PAGE gels. Inhibition of cleavage can be similarly confirmed. Inhibition of the VEEV nsP2 cysteine protease by the covalent inhibitor, E64d, is shown in lane 4.

FIG. 2F shows the CFP/YFP substrates [SEQ ID NOs: 2, 3, 16, 17] with or without treatment a recombinant CHIKV nsP2 protease [SEQ ID NO: 29]. The recombinant CHIKV nsP2 protease [SEQ ID NO: 29] preferentially cut the SFV substrates; both CHIKV and SFV are Old World alphaviruses. The recombinant VEEV nsP2 protease showed broader substrate specificity and was capable of cleaving both Old World and New World sequences, whereas the CHIKV nsP2 protease cut only Old World substrates.

FIG. 4D shows the calculated molecular weights (MW) of each isoform and cleavage product. FIG. 4E is a replicate showing the 6 and 24 h time points. TRIM14 cleavage product was visible in the VEEV-infected cells, but was less apparent in the EEEV and WEEV infected cells consistent with the in vitro results using CFP-TRIM14-YFP (FIG. 2B).

DETAILED DESCRIPTION

Definitions

Figures 1A, 1B:
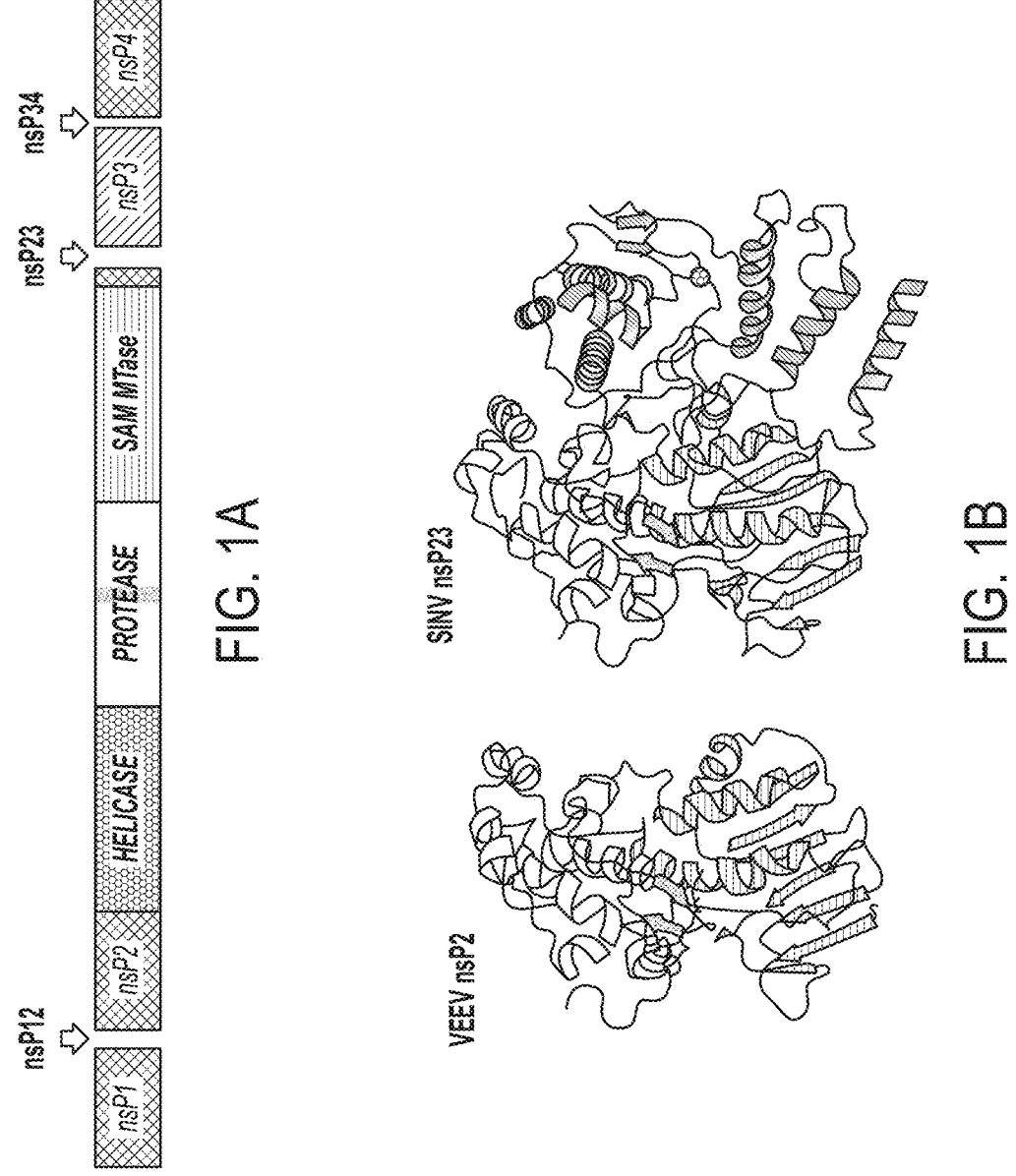

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used herein, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

As used herein, "suspected of being infected" is meant to be interpreted very broadly to compass instances where an infection is virtually certain to those where it is not believed that an infection exists.

Overview

Described herein are a novel bioinformatic method and recombinant fluorescence resonance energy transfer (FRET) substrates for proteases of Group IV viruses (cleavage of which can be detected in several ways). The substrates containing the cleavable human sequences can be produced in *E. coli* and used in a plate reader to monitor cleavage in real time (continuous assay), in a mass spectrometer, or in an SDS-PAGE gel (discontinuous assay) for the identification of protease inhibitors that are capable of effectively competing with these host-relevant substrates. The substrates represent new techniques for the detecting viral protease activity in a specific host (e.g. human), and can further serve to help discover inhibitors of the proteases for therapeutic use.

Alphaviruses are (+)ssRNA viruses and belong to the Togaviridae family of Group IV. Group IV contains 33 families and includes the Coronaviridae, Picornaviridae, and Flaviviridae among others. Venezuelan equine encephalitis virus (VEEV) is a New World alphavirus that belongs to Group IV. The other New World alphaviruses, eastern (EEEV) and western (WEEV) equine encephalitis viruses, share high sequence identity (68%) with VEEV, but are significantly more lethal in humans, with mortality rates of 36% and 10%, respectively (2; 4; 8; 10; 11). The Old World alphaviruses such as Chikungunya (CHIKV), Sindbis (SINV), and Semliki Forest (SFV) viruses are more commonly associated with fever, arthralgia, skin rashes, and malaise (12). What accounts for the differences in virulence and pathogenicity is not well delineated.

During alphaviral replication, recognition of double stranded RNA replication intermediates in the cytoplasm by RIG-I or MDA-5 triggers the mitochondrial antiviral signalosome (MAVS) and results in the rapid production of type I interferons (IFN) and proinflammatory cytokines (17; 18). IFN plays an important role in limiting acute alphaviral infections (17-19). IFN can protect uninfected cells from infection and create an antiviral state to prevent further alphaviral replication (20). IFN-stimulated genes (ISG) can inhibit the replication of CHIKV, SINV, and VEEV and other viruses (21-24). Alphaviruses utilize multiple redundant mechanisms to antagonize the IFN response (25). To evade the innate immune responses alphaviruses shut off host cell transcription and translation, typically within hours post-infection (14; 23), to prevent the expression of ISG.

VEEV viral particles are highly resistant to desiccation and can be stably lyophilized and aerosolized (1) which has implications for its use as a potential bioweapon. Inhaled virus can disseminate into the brain via the olfactory neurons (2-4), and symptoms can occur within 28-33 hours in humans (5-8). Acute alphaviral infections are typically resolved by the innate and adaptive immune responses. Only ~1% of human VEEV infections result in lethal encephalitis; however, neurological symptoms occur in approximately 14% (5; 8; 9).

Alphaviruses are known to utilize their nonstructural and structural proteins to transiently suppress the innate immune responses in order to replicate, and the mechanisms of suppression differ among alphaviruses (13; 14). Some similarities in virulence may have arisen from genetic recombination events (e.g. WEEV which has EEEV-like encephalogenic properties is thought to have arisen from a SINV-like and EEEV-like ancestor (15)). Virulence differs in host species, as the name suggests the mortality rates of EEV infections are significantly higher for equine than humans and can range from 40-90% (16).

The nonstructural proteins (nsPs) play essential roles in replication, but can also play secondary roles in IFN-antagonism. The role of the nsPs in IFN-antagonism can be either enzymatic or non-enzymatic (e.g. binding). The nsP2 of alphaviruses contains an N-terminal domain, a helicase, a papain-like protease, and an S-adenosyl-L-methionine-dependent RNA methyltransferase (SAM MTase) domain (FIG. 1A). The nsP2 of Old World alphaviruses, SINV, SFV, and CHIKV, can inhibit transcription in a manner that is independent of its protease activity, but reliant on its helicase activity (26). These nsP2 proteins induce the rapid degradation of Rpb1, a catalytic subunit of the RNA polymerase II complex, through nsP2-mediated ubiquitination. The ubiquitination of Rpb1 depends on the enzymatic activity of the Old World nsP2 helicase, but also on the integrity of the SAM MTase domain. Mutations within these domains were shown to abolish Rpb1 degradation (26). The transcriptional shut-off mechanisms are known to differ for Old and New World alphaviruses (27). In cells infected with the New World alphavirus, VEEV, transcriptional shutoff is mediated by a 39-residue sequence at the N-terminus of the capsid protein; the capsid is thought to partially obstruct the nuclear pore complex to block host mRNA export (28; 29). While these viruses can effectively counter the innate immune responses using these shutoff mechanisms, intrinsic immune factors pose additional challenges since these proteins are present prior to viral infection and sufficient quantities of viral proteins (e.g. capsid) may not be present to override their effects early in infection. Catalytic amounts of the viral enzymes may thus be important for establishing infection.

Viral proteases may also be partially responsible for the virus-induced phenotypes (95) as some of the identified cleavable human sequences were found in proteins that have not been previously implicated in antiviral responses, e.g. a human cardiac myosin sequence found in MYH6 and MYH7 was cut by the SARS-CoV-2 (severe acute respiratory syndrome coronavirus 2) papain-like protease (PLpro) (95). Moreover, sarcomere fragmentation associated with SAES-CoV-2 infection was observed in infected human heart cells (100), likely due to viral protease activity.

As described below, the VEEV nsP2 protease was found by the inventors to cleave human TRIM14 and is likely to antagonize the production of interferon. The inventors also demonstrated the cleavage of other host proteins by the Group IV viral proteases of Zika virus (ZIKV, Flaviviridae), SARS-CoV-2 and MERS (Middle Eastern respiratory syndrome, Coronaviridae). The PLpro of SARS-CoV-2 was able to cleave a sequence in human Protein S (PROS1), an anti-coagulant protein that prevents blood clots, a sequence in human FOXP3 (forkhead protein P3), a transcription factor in $T_{regulatory}$ ($T_{reg}$) cells, a sequence in the human cardiac myosins MYH6 and MYH7, and a sequence in human epidermal growth factor receptor 4, erbB4 (HER4).

The preferred substrates of the SARS-CoV-2 PLpro were those containing the cardiac myosin sequences [SEQ ID NOs: 7, 8]. The MERS PLpro showed minor cleavage of the cardiac myosin sequences, but similar levels of cleavage of Protein S, FOXP3 and erbB4 (HER4) substrates. These substrates were systematically identified using the new bioinformatics method developed by the inventors and their cleavage by the viral proteases was confirmed in vitro (FIG. 8C) (95). The mechanism has implications with regard to sequence specific techniques to "silence" expressed proteins by analyzing the substrate specificities of the viral proteases. Bacterial proteases such as the zinc metalloproteases of botulinum neurotoxins have been shown to cut host proteins intracellularly and these proteases have been applied therapeutically. The inventors have demonstrated cleavage of these human proteins in vitro using recombinant viral proteases produced in large scale from *E. coli*, and with tissue lysates or purified full length proteins (95). The inventors have also demonstrated cleavage of TRIM14 in cells using live virus (VEEV).

Prior methods to reduce protein concentrations in a cell include CRISPR/Cas9 and RNAi/RISC. Because these methods work at the level of DNA and RNA, respectively, they must be applied prior to protein expression and thus cannot alter the concentrations of proteins that have already been expressed in a cell or have entered into a cell (e.g. protein toxin). The method of post-translational silencing using a viral protease enables transient silencing.

Figure 6:
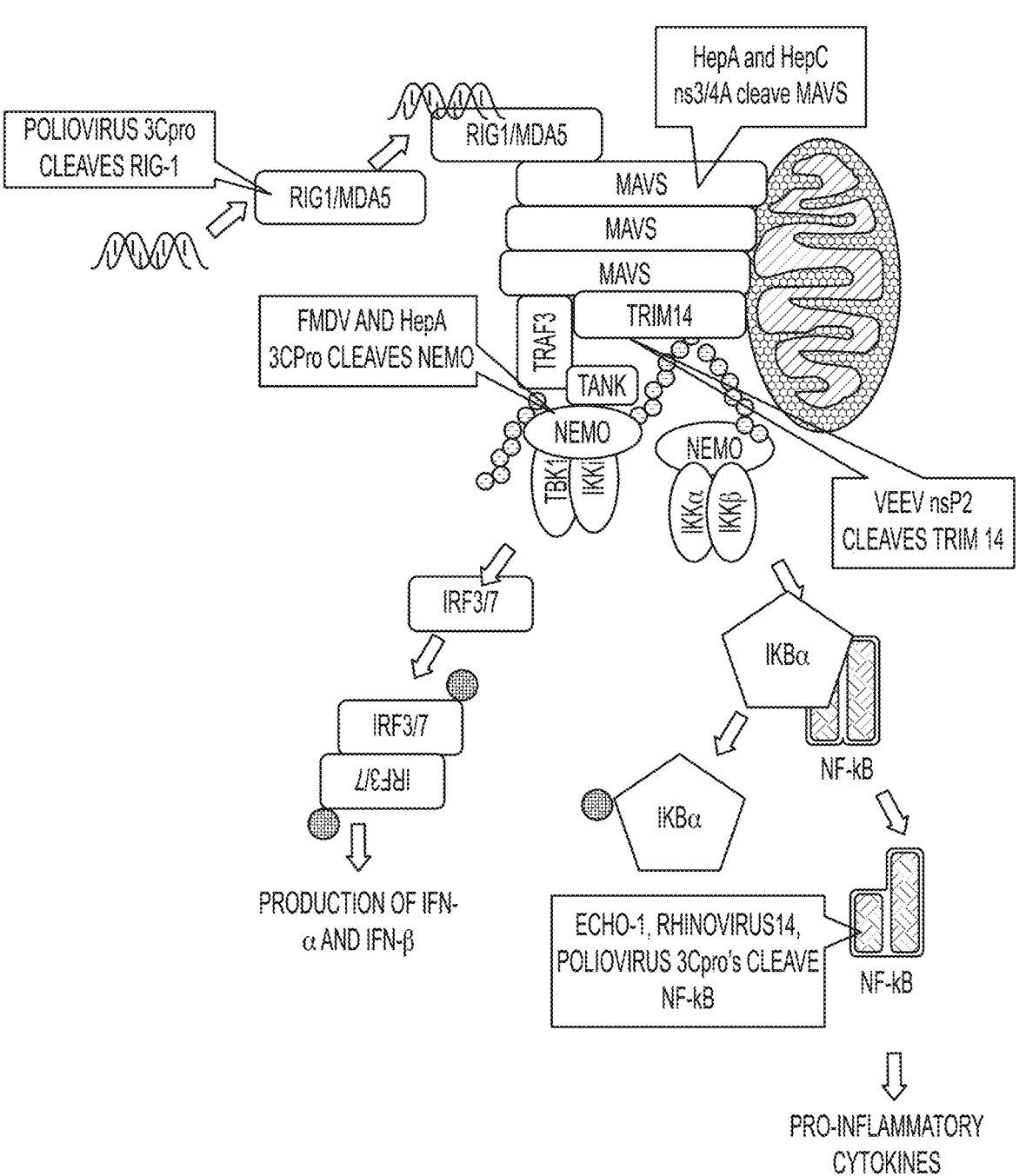
FIG. 6 illustrates how several Group IV (+)ssRNA viral proteases cleave components of the mitochondrial antiviral signalosome (MAVS). The MAVS signaling cascade proposed by Zhou, et al is shown (32). The MAVS signalosome triggers the production of interferon (IFN) and pro-inflammatory cytokines. The VEEV nsp2 cysteine protease cleavage site in TRIM14 is located before the ubiquitination site. Cleavage of the proteins involved in the signalosome would likely disrupt the production of IFN and the innate immune response.

The alphaviral nonstructural protein 2 (nsP2) cysteine proteases (EC 3.4.22.-) are involved in the proteolytic processing of the nonstructural (ns) polyprotein. After examining the substrate specificities of the VEEV nsP2 cysteine protease, a new host substrate of the VEEV nsP2 protease, human TRIM14, was identified. The TRIM14 protein is a component of the mitochondrial antiviral-signaling protein (MAVS) signalosome (FIG. 6). The same amino acid sequences, termed short stretches of homologous host-pathogen protein sequences (SSHHPS), are present in both the viral nonstructural polyprotein and the host's proteome.

It is contemplated that these findings could be employed to facilitate post-translational silencing at the level of protein (removal of existing proteins) as a protein analog to CRISPR/Cas9 and RNAi/RISC. The natural or recombinant viral proteases could be expressed in cells or in animals to sequence-specifically cut their identified host protein substrates (Table 2). These viral enzymes (natural or recombinant) could be used therapeutically similar to the Botulinum neurotoxins. Alternatively, the identified cleavage site sequences in these human proteins could be introduced into transgenic animals or into cell lines to recapitulate the effects of the viral protease in an animal model or cells. This system relies on the identification of the SSHHP sequences using bioinformatics methods and an appropriate recombinant or natural viral protease (as opposed to a nuclease) that cleaves them. It is further contemplated that the presence or absence of a viral infection could be detected by analysis of the cleavage products of the viral proteases, or the consequent downstream effects produced from silencing using the appropriate viral nsP protease.

Also described herein (see Table 2) are a number of peptide sequences operable as recognition sites of a Group IV viral protease (SEQ ID NOs: 2-22) or as uncleavable control sequences (SEQ ID NO: 23, 24), optionally with a FRET pair of fluorophores at either end thereof. These are useful in detecting activity of the proteases, with a readout available optically, or via a separation method such as SDS-PAGE or mass spectroscopy. In various aspects, the FRET pair of fluorophores are EDANS (5-((2-Aminoethyl) amino)naphthalene-1-sulfonic acid) and DABCYL (4-(dimethylaminoazo)benzene-4-carboxylic acid); or yellow fluorescent protein (YFP) and a cyan fluorescent protein (CFP), or other variants of green fluorescent protein.

Using the peptides operable as recognition sequences to detect enzyme activity enables the diagnosis and subsequent treatment of infection by these viruses, and furthermore allows for in vitro screening of small molecule inhibitors of the viral proteases for drug discovery.

DESCRIPTION

The present inventors hypothesized that the alphaviral protease cleavage sites may share homology with regions of human proteins and that the virus may use these short stretches of host sequences to recognize host proteins and then cut them as another mechanism of IFN-antagonism. The viral proteases not only recognize proteins involved in generating the innate immune responses, but other proteins that have not been implicated in immune responses. These other protein targets may represent the "off-targets" of these viral proteases. These off-target cleavages had relationships to the observed symptoms of the virus. The VEEV nsP2 substrate specificities were previously characterized by the inventors using kinetic, mutational and structural studies (30. The inventors examined potential host protein targets of the nsP2 protease by searching the human proteome for proteins sharing sequence identity with the nsP12, nsP23, and nsP34 cleavage site sequence motifs. One human protein, TRIM14 (also known as Pub (31)), sharing six identical residues to an alphaviral nsP12 cleavage site, was identified as a substrate of the VEEV nsP2 viral protease. Consistent with in vitro assay results—TRIM14 cleavage could be detected in immunoblots of VEEV-infected cell lysates.

Figure 8A:
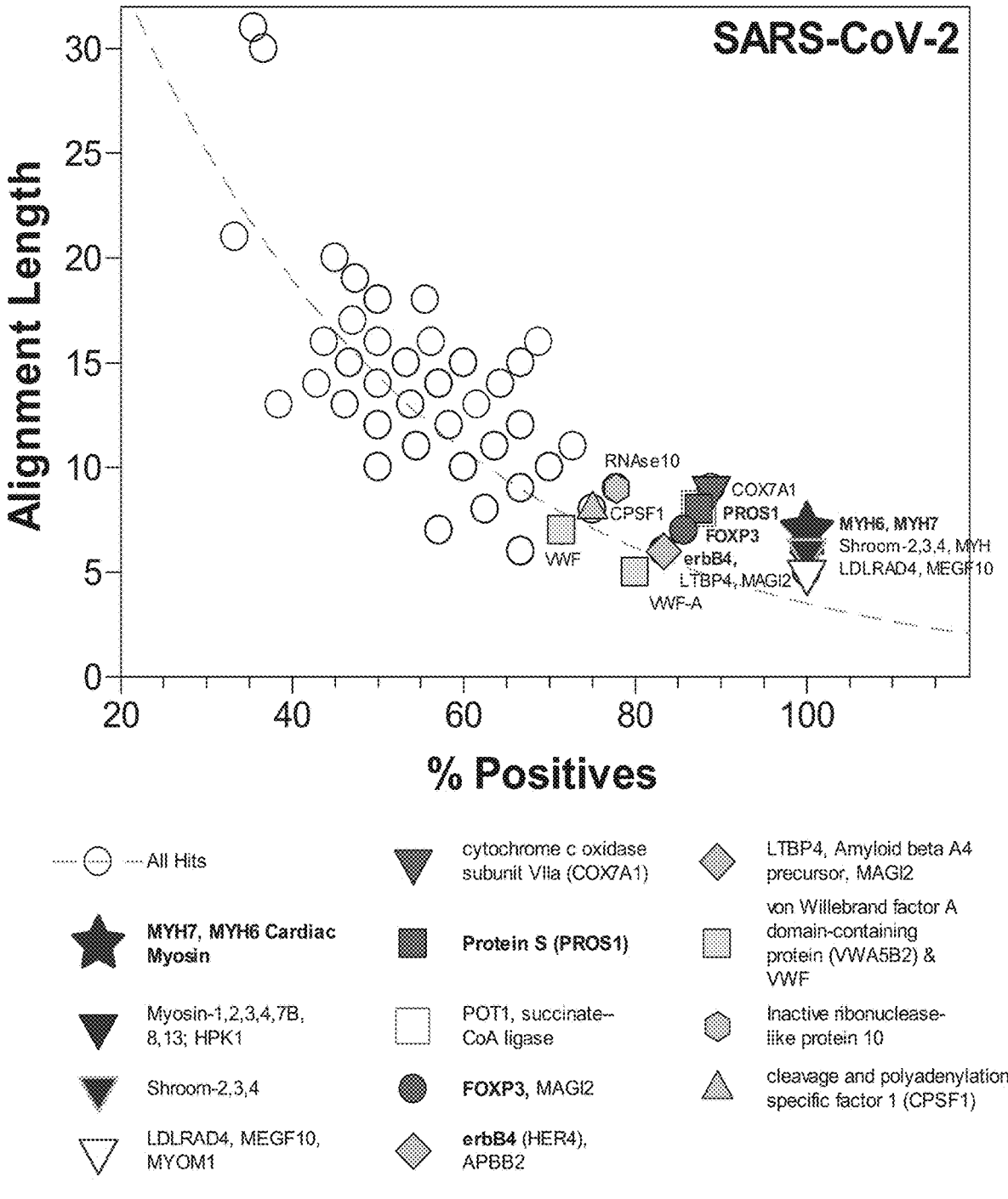
FIG. 8A provides an examples of the new bioinformatic method developed by the inventors and the graphical method that separates the most likely host protein substrates recognized by the viral protease.
Figure 8B:
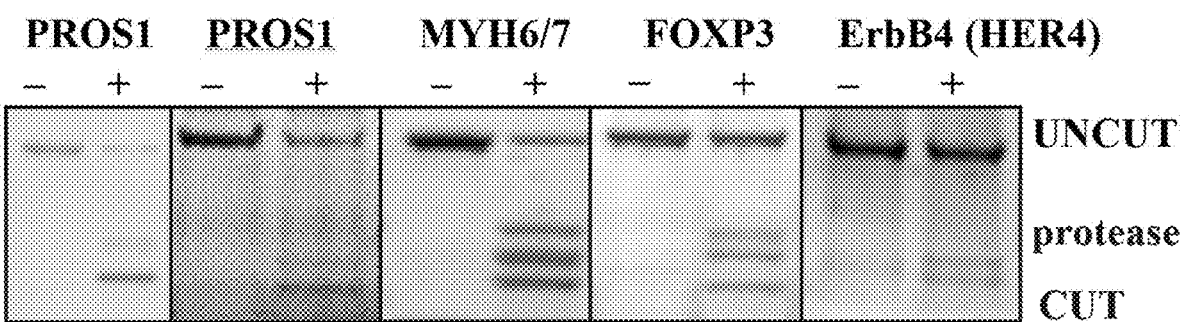
FIG. 8B shows the cleavage of the CFP-YFP substrates containing SEQ ID NOs: 8, 9, 10, 12 by the SARS-CoV-2 recombinant protease (SEQ ID NO: 26). From left to right, CFP-PROS1-YFP [SEQ ID NO: 9] cleavage is shown in an immunoblot probed with an anti-His-tag antibody (#70796), then in a SDS-PAGE gel, CFP-MYH6/7-YFP [SEQ ID NO: 8] substrate cleavage in SDS-PAGE gel, CFP-FOXP3-YFP substrate [SEQ ID NO:12] cleavage in SDS-PAGE gel, and CFP-ErbB4 (HER4)-YFP [SEQ ID NO: 10] cleavage in SDS-PAGE gel.
Figure 8C:
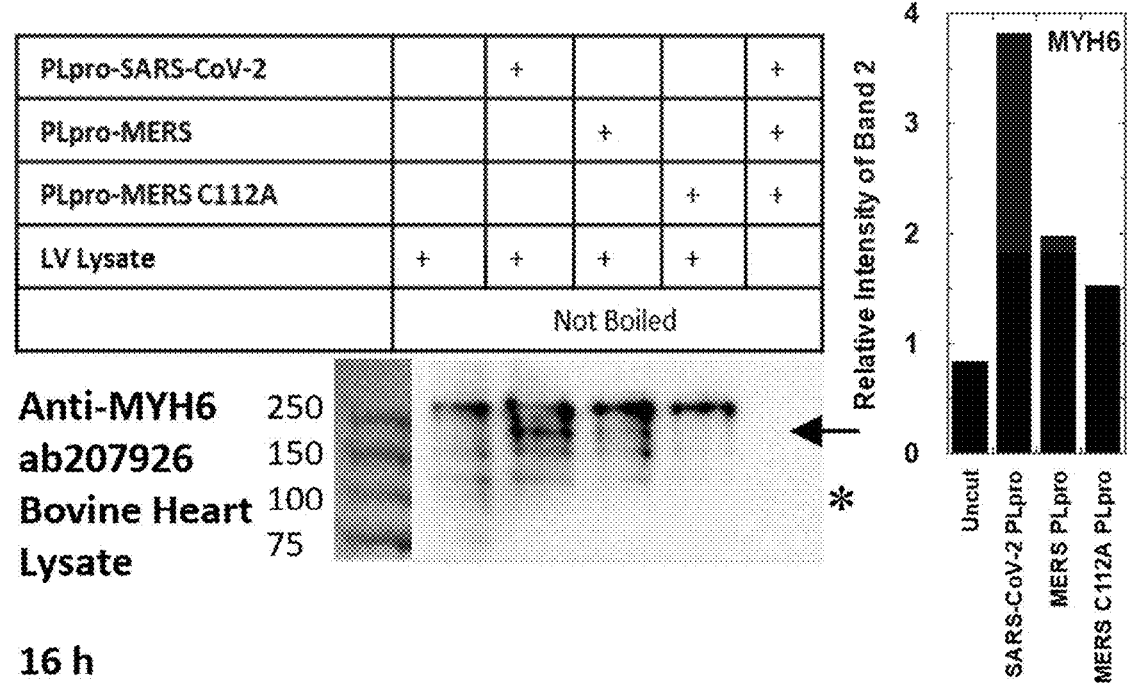
FIG. 8C shows confirmation of cleavage of cardiac myosin in an immunoblot probed with an anti-MYH6 antibody. Bovine heart extracts were incubated with or without the recombinant SARS-CoV-2 protease and a new cleavage product band was identified (Lane 3).
Figure 9A:
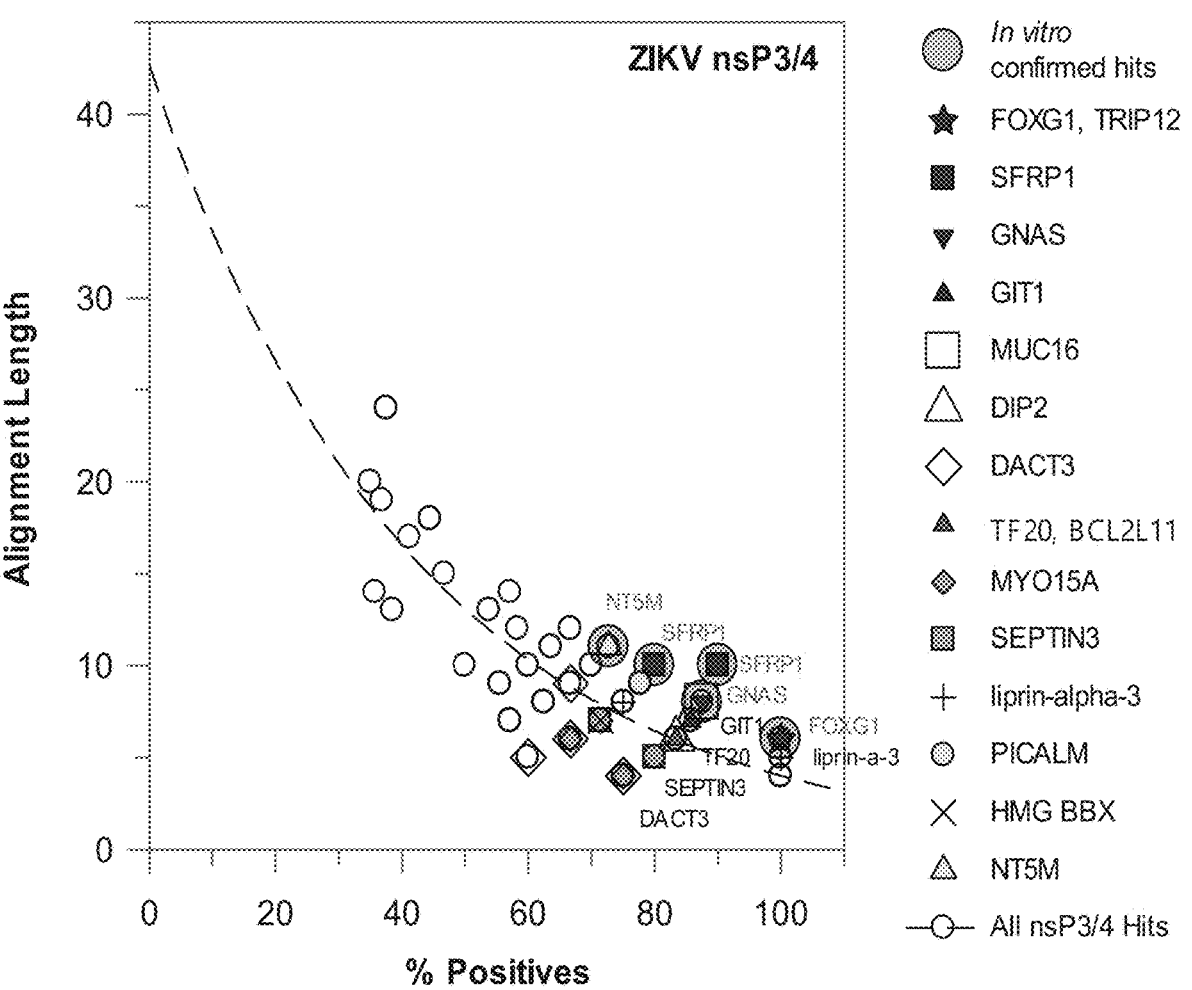
FIG. 9A shows a graphical representation of the pattern-hit initiated basic local alignment search tool (PHI-BLAST) hits for the Zika viral protease using the new bioinformatic method.
Figure 9B:
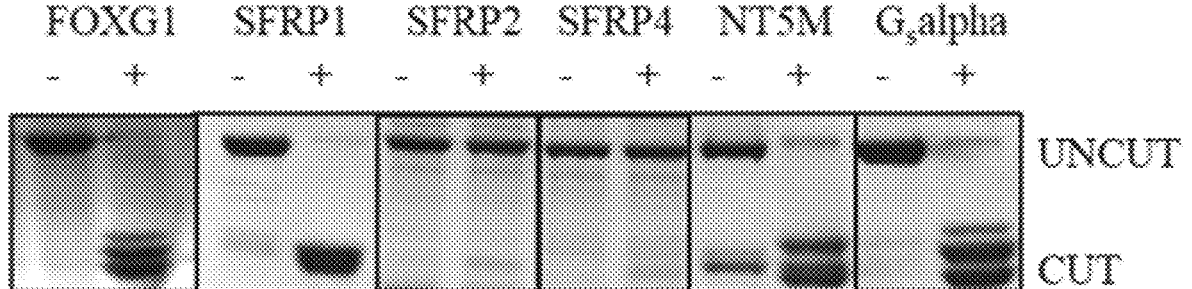
FIG. 9B shows the cleavage of the substrates containing the FOXG1, SFRP1, NT5M and Gs, alpha substrates separated by SDS-PAGE [SEQ ID NOs: 19-22] by the recombinant Zika viral protease [SEQ ID NO: 28].

Other recombinant viral proteases appropriate for drug discovery (SARS-CoV-2 PLpro, ZIKV ns2B/ns3, and MERS PLpro) were analyzed by the inventors [SEQ ID NO: 25, 26, 27, 28, 29] and the corresponding host substrates were created [SEQ ID NO: 7-22] (FIGS. 8, 9). Cleavage was confirmed by mass spectrometry, immunoblot, or SDS-PAGE, or a combination of these methods. The FRET CFP-YFP substrates created by the inventors and their corresponding viral proteases are shown in Tables 1 and 2.

TRIM14 is a tripartite motif protein (TRIM) and was recently shown to function as an adaptor protein in the MAVS signalosome (32; 33). Stable overexpression of TRIM14 has been shown to inhibit alphaviral replication by 34 logs 24 h post-infection using SINV (34). TRIM14 overexpression also increased the transcription of IFNs and interferon stimulated genes (33). The viral proteases' ability to cleave a protein involved in the production of IFN appears to be a common antagonistic mechanism used by this and other Group IV viral proteases. We discuss the similarities of this silencing mechanism with those of CRISPR/Cas9 and RNAi/RISC.

At least eight other Group IV (+)ssRNA viral proteases have been shown to cleave components of the MAVS signalosome to antagonize IFN production suggesting that the assimilation of these short cleavage site motif sequences to host protein sequences may represent an embedded mechanism of IFN antagonism. This interference mechanism shows several parallels with those of CRISPR/Cas9 and RNAi/RISC, but with a protease recognizing a protein sequence common to both the host and pathogen.

The other viral proteases tested, SARS-CoV-2 PLpro, MERS PLpro, and ZIKV ns2B/ns3 protease cut a variety of host substrates, including proteins that have not been previously implicated in immune response generation. For example, MYH6, MYH7, and PROS1 were cut by the SARS-CoV-2 PLpro; PROS1 was also cut by the MERS PLpro. Immune response related protein substrates were also identified such as FOXP3 and ErbB4 (HER4). These proteins were cut by the SARS-CoV-2 and MERS PLpro enzymes (FIG. 8B).

EXAMPLES

Example 1: Monitoring Cleavage of Human TRIM14 by the VEEV nsP2 Protease In Vitro and in Virus-Infected Cells The sequences N- and C-terminal to the scissile bond that were recognized by the VEEV nsP2 cysteine protease were previously identified using a set of peptide substrates. The 25-residue substrates containing P19-P6' (Schechter and Berger nomenclature (35)) produced the lowest $K_m$ values (30). A BLAST search (36) using the nsP2 cleavage sites and the human proteome uncovered one protein, TRIM14, which had a high level of sequence identity to the VEEV nsP12 cleavage site. The nsP12 cleavage site QEAGA↓G (SEQ ID NO: 1) is highly conserved among the more virulent New World alphaviruses, VEEV/EEEV/WEEV, but not in the Old World alphaviruses such as SINV, SFV, and CHIKV (FIG. 1C).

Figure 2A:
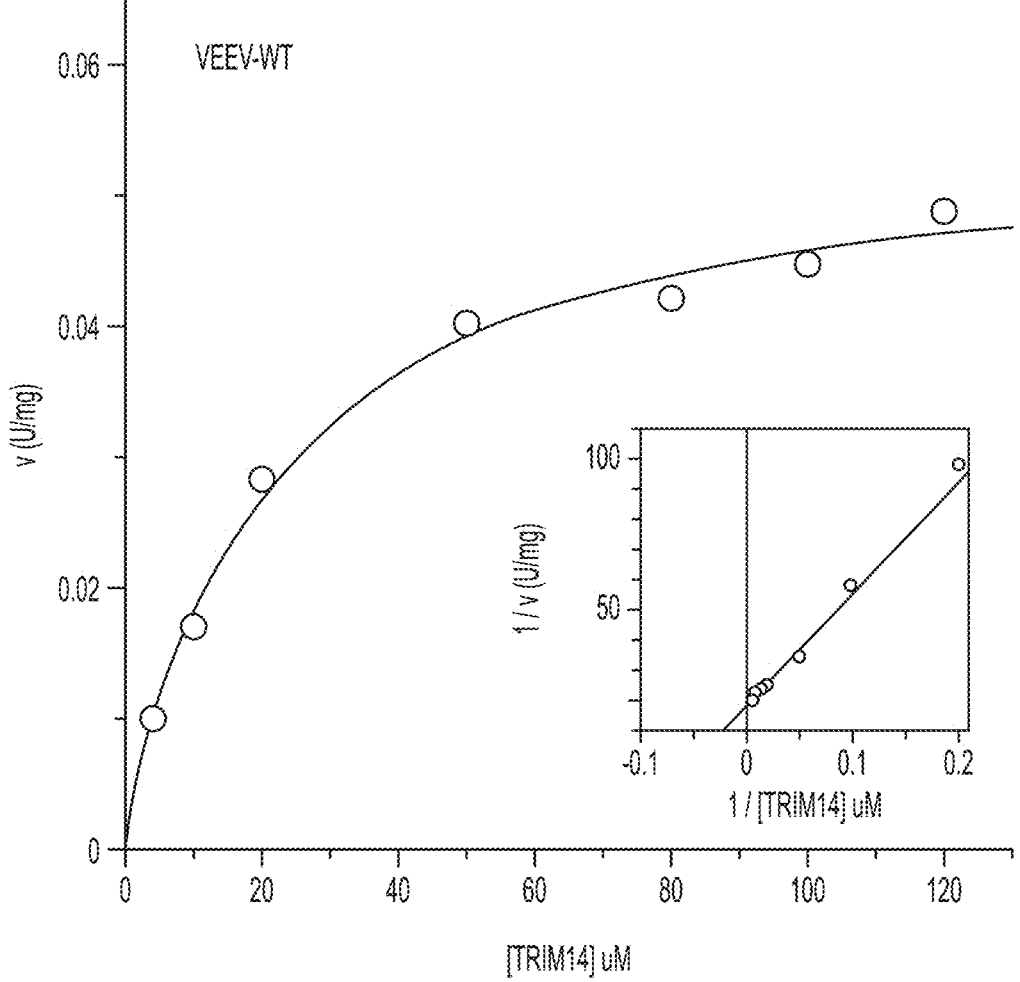
Figure 2B:
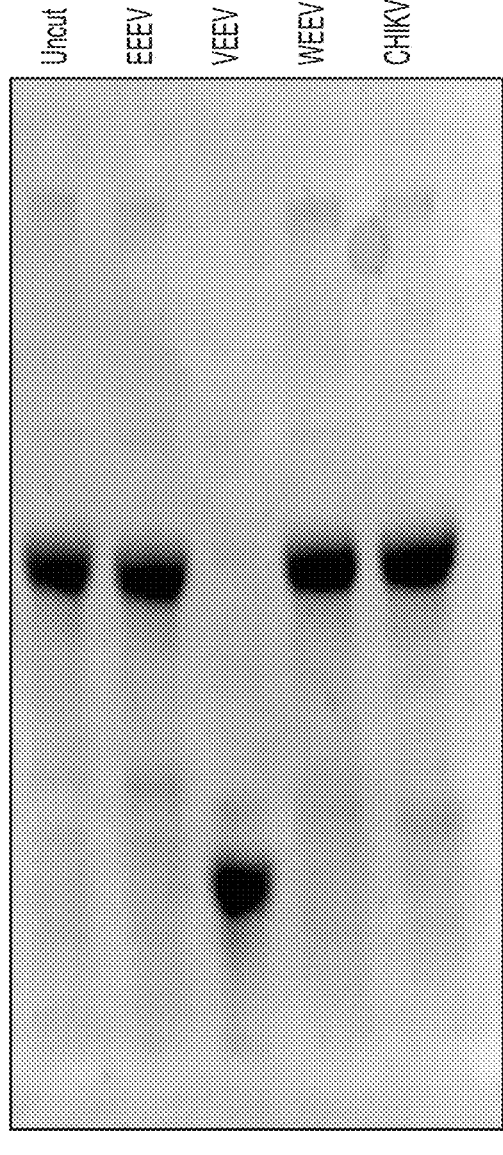
Figure 2C:
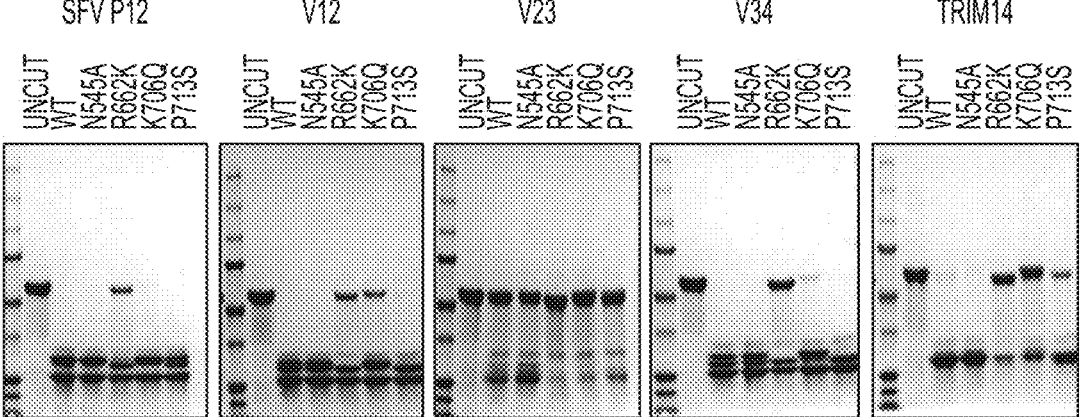
Figure 2D:
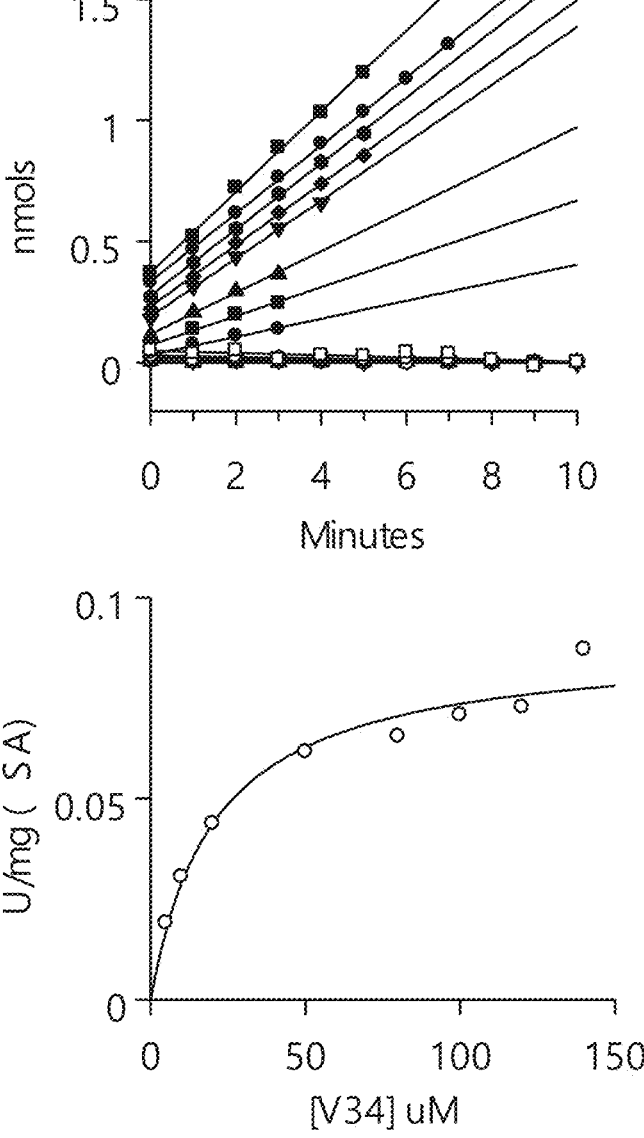
Figure 2E:
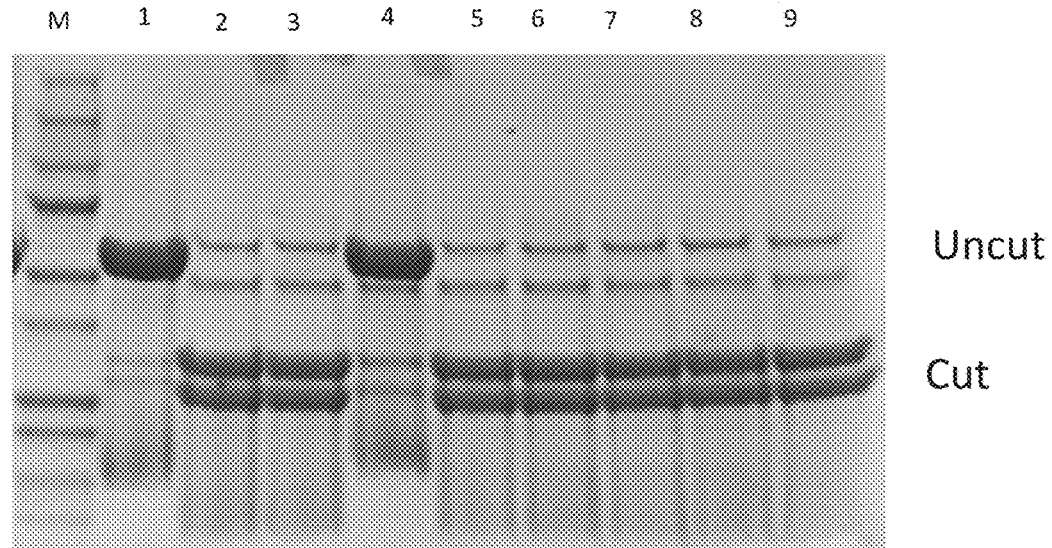

Using a cyan and yellow fluorescent protein (CFP-YFP) substrate containing 25-amino acids of the human TRIM14 protein, the purified VEEV nsP2 protease was found to cleave the TRIM14 substrate [SEQ ID NO: 4] (FIG. 2A, Table 1), but no cleavage occurred with other recombinant viral proteases (FIG. 2B). Cleavage was confirmed by SDS-PAGE, and the effects of site-directed mutagenesis of the protease on the cleavage of the CFP-TRIM14-YFP [SEQ ID NO: 4] substrate were similar to those observed for the substrate containing the VEEV nsP12 cleavage site (V12) [SEQ ID NO: 2] suggesting similar enzyme and substrate contacts (FIG. 2C). To continuously assay the recombinant VEEV nsP2 protease, cleavage can be monitored in a plate reader. Hydrolysis of the substrate containing the VEEV nsP34 cleavage site [SEQ ID NO: 3] is shown in (FIG. 2D). The substrates can be used two ways—in a plate reader for a continuous assay or in an SDS-PAGE gel for a discontinuous assay (without fluorescence). This enables the analysis of small molecule protease inhibitors (FIG. 2E). Some overlap in substrate specificities was observed for the VEEV and CHIKV nsP2 proteases; both are able to cleave the Old World SFV nsP12 substrate [SEQ ID NO: 16 and 17] (FIG. 2F) (30. Substrates that can be utilized by both proteases may be useful for broad spectrum inhibitor analysis.

Figure 3A:
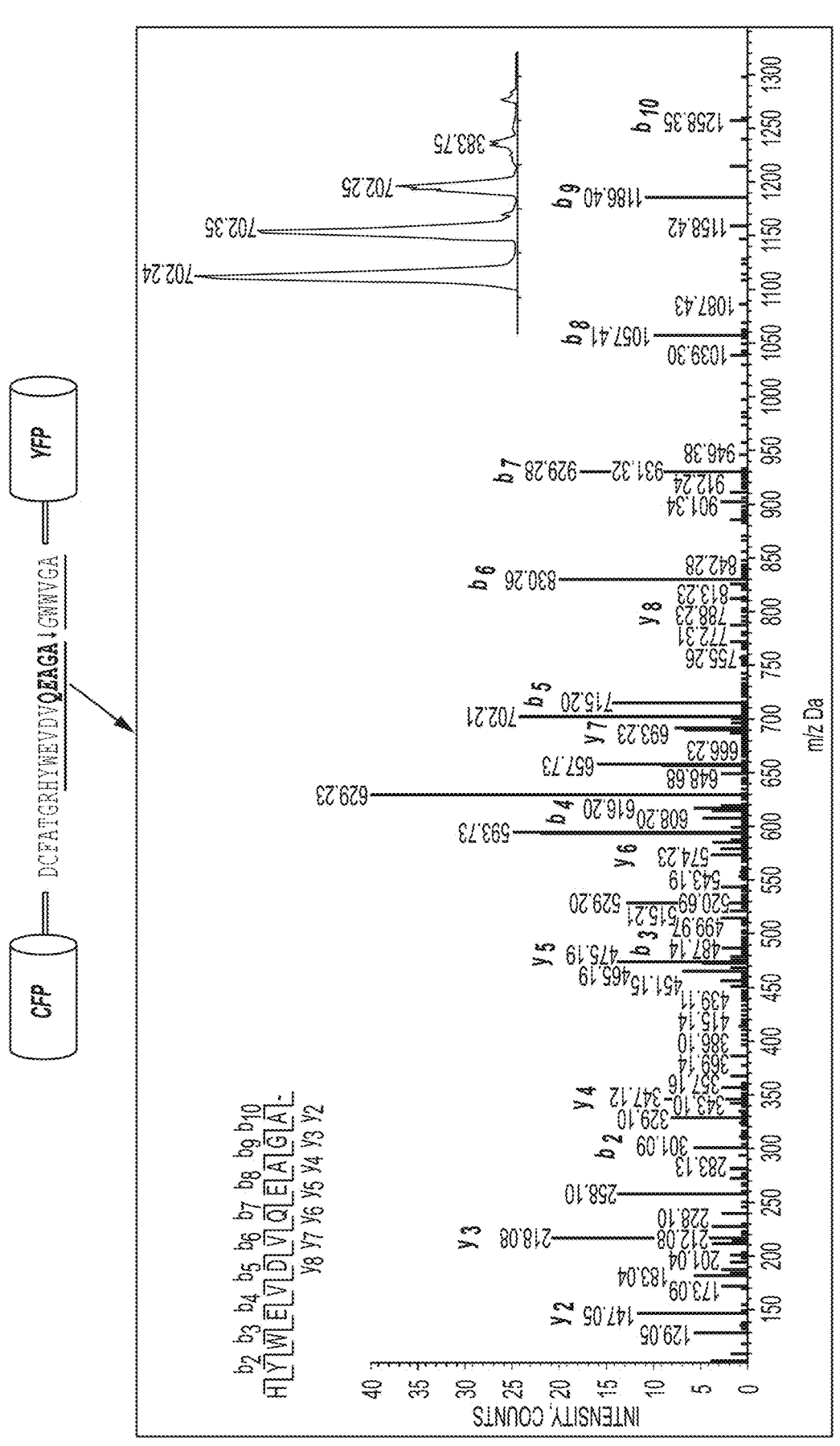
FIGS. 3A and 3B illustrates the mass spectra of the CFP-TRIM14-YFP proteolytic products. Proteolytic products of the CFP-TRIM14-YFP 25-residue substrate [SEQ ID NO: 4] after cleavage by the VEEV nsP2 cysteine protease [SEQ ID NO: 25] were separated by SDS-PAGE to confirm the scissile bond. The bands were excised, extracted, trypsinized, and identified by tandem mass spectrometry to verify the specificity of the protease and cleavage site. Annotated MS/MS spectra of the HYWEVDVQEAGA and GWWVGAMVS are shown in FIGS. 3A and 3B, respectively, and confirm the sequence specific cleavage of the substrate by the recombinant protease. For simplicity only singly charged fragments were annotated. All predicted singly charged fragment ions were found.
Figure 3B:
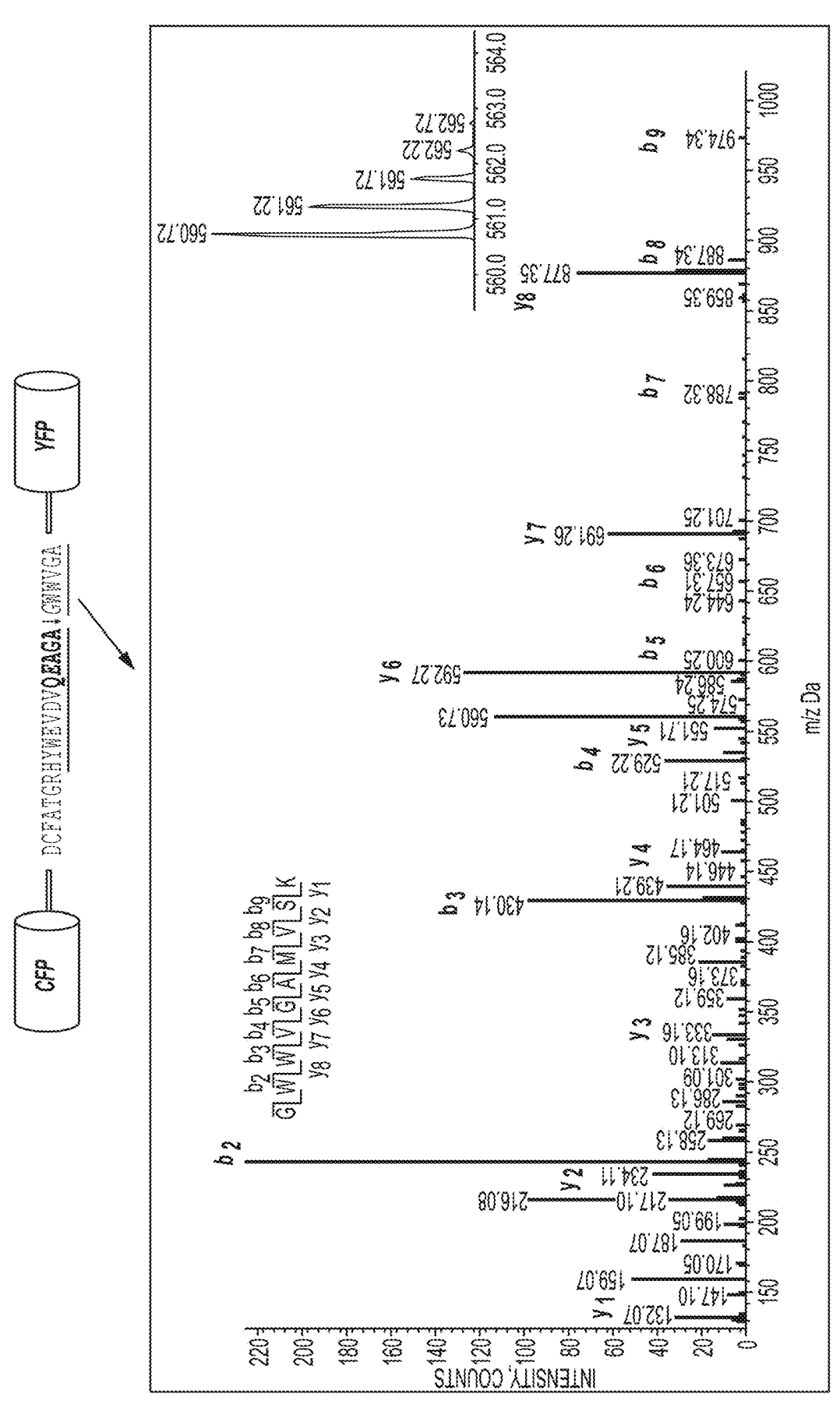

For the recombinant VEEV nsP2 protease [SEQ ID NO: 25], the cleavage site in the CFP-TRIM14-YFP substrate was confirmed by tandem mass spectrometry (FIGS. 3A and 3B), and cleavage occurred at the expected site at QEA-GA↓G [SEQ ID NO: 1]. The tryptic peptides of both parts of the substrate were identified.

Steady state kinetic parameters were measured to determine if the $K_m$ and $V_{max}$ measured with the CFP-TRIM14-YFP 25-residue substrate [SEQ ID NO: 4] and recombinant VEEV nsP2 protease [SEQ ID NO: 25] and were similar to those obtained with substrates containing the viral cleavage sites found in the polyprotein [SEQ ID NO: 2 and 3] (FIG. 2A, Table 1). The $K_m$ and V obtained with the wild type (WT) VEEV nsP2 protease and the TRIM14 substrate were comparable to those obtained with the nsP12 and nsP34 substrates. The length of the substrate was also varied and 25-, 22-, and 19-residue substrates were tested (Table 1). As the length of the region N-terminal to the scissile bond decreased, an increase in the $K_m$ and $V_{max}$ was observed consistent with weaker binding and faster product release.

To determine if the cleavage was specific to the VEEV nsP2 protease, the recombinant proteases of VEEV, EEEV, WEEV and CHIKV were expressed and purified. With the 25-residue TRIM14 substrate, complete cleavage of the substrate (50 μM) by the VEEV protease (5 μM) was visible after 24 h at 23±3° C. by SDS-PAGE (FIG. 2B); however, with the shorter CFP-TRIM14-YFP substrates the purified CHIKV, EEEV, and WEEV nsP2 proteases only produced low levels of cleavage product even after extensive incubation (64 h, 23±3° C.) (VEEV>WEEV>EEEV>CHIKV) (data not shown). The corresponding viral cleavage sites were also digested for relative comparison since the proteases from different viruses differ in activity. Only the VEEV nsP2 cysteine protease consistently cut all of the CFP-TRIM14-YFP substrates.

Regions beyond P5 were examined to understand why the recombinant EEEV and WEEV nsP2 proteases cut CFP-TRIM14-YFP poorly. Based on the $K_m$ values (Table 1) the P13-P19 residues of the substrate appear to make additional contacts to the enzyme. In PDB SEZQ the P17 residue (Ser-778) within the helix of the symmetry related molecule is within hydrogen bonding distance to the backbone NH and C=O of the papain-like protease domain residue Met-555. Met-555 is conserved in the VEEV/EEEV/WEEV nsP2 cysteine proteases. The P19-P16 residues of the substrates differ in charge and flexibility in the New World polyproteins and may be recognized differently by these closely related proteases: "VEEP" in VEEV nsP12; "VDKE" in EEEV nsP12; and "IEKE" in WEEV nsP12. The homologous residues in TRIM14 are "DCFA." Alternatively, the recombinant EEEV and WEEV proteases may require an additional region of the nsP to attain full activity similar to the ZIKV ns2B-ns3 protease.

Cleavage of the CFP-TRIM14-YFP substrate by mutants of the protease was examined to confirm the models of the

TABLE 1

Steady state kinetic parameters for the VEEV nsP2 cysteine protease measured in 50 mM HEPES pH 7.0 at room temperature (R.T.) and the FRET substrates.

| Substrate | | Length | $V_{max}$ (U/mg) | $K_m$ (μM) |
|---|---|---|---|---|
| CFP-V12-YFP | VEEPTLEADVDLMLQEAGA↓GSVETP (SEQ ID NO: 2) | 25 | 0.059 ± 0.003 | 12 ± 3 |
| CFP-V34-YFP | TREEFEAFVAQQQRFDAGA↓YIFSSD (SEQ ID NO: 3) | 25 | 0.089 ± 0.005 | 21 ± 4 |
| CFP-TRIM14-YFP | DCFATGRHYWEVDVQEAGA↓GWWVGA (SEQ ID NO: 4) | 25 | 0.056 ± 0.002 | 21 ± 2 |
| | ATGRHYWEVDVQEAGA↓GWWVGA (SEQ ID NO: 5) | 22 | 0.0080 ± 0.0003 | 26 ± 4 |
| | RHYWEVDVQEAGA↓GWWVGA (SEQ ID NO: 6) | 19 | 0.012 ± 0.002 | 50 ± 20 |

A computer model was created of the binding interactions of TRIM14 with the VEEV nsP2 cysteine protease in order to gain insight into the structural basis of substrate specificity. Like the New World alphaviral substrates, TRIM14 contains a Glu at position P4 which may explain why no cleavage of TRIM14 was observed with the Old World CHIKV nsP2 protease. The CHIKV nsP2 protease contains an Arg at position P4. In the nsP12 cleavage site, the P1'-P6' residues are identical in sequence for VEEV/EEEV/WEEV, as are the P1-P5 residues (amino acid residues in a substrate undergoing cleavage are designated P1, P2, P3, P4 etc. in the N-terminal direction from the cleaved bond, while the residues in C-terminal direction are designated P1', P2', P3', P4'. etc.). This suggests that residues beyond P5 are important for recognition of the TRIM14 substrate. To understand why the 25-amino acid substrate led to the lowest $K_m$ and highest $k_{cat}$, the inventors examined their previously determined crystal structure of the free VEEV nsP2 protease, PDB SEZQ (30). The crystal structure contains the C-terminal P2-P19 residues (Leu-776-Ala-792) of the VEEV nsP23 cleavage site; the P10-P19 residues are helical and are packed against the protease domain in the crystal. The P8-P9 residues are directed into the cleft formed by the protease and SAM MTase domains (data not shown). Chou-Fasman secondary structure predictions suggest that the nsP12 and nsP34 substrates may contain helical regions within the P1-P19 residues.

VEEV nsP2 cysteine protease (FIG. 2C). The K706Q mutation affected the cleavage of V12 and TRIM14 consistent with the disruption of substrate binding interactions in the predicted S4 subsite. The P4 residues (Glu) are the same in both of these substrates. The purity of the VEEV nsP2 protease was also examined using the C477A variant. Strauss et al. had previously shown that the nonstructural polyprotein was not cut by any host enzymes in eukaryotic cells (32); similarly, non-specific cleavage of these protein substrates was not observed with the CFP-YFP substrates expressed and purified from E. coli.

Figure 4A:
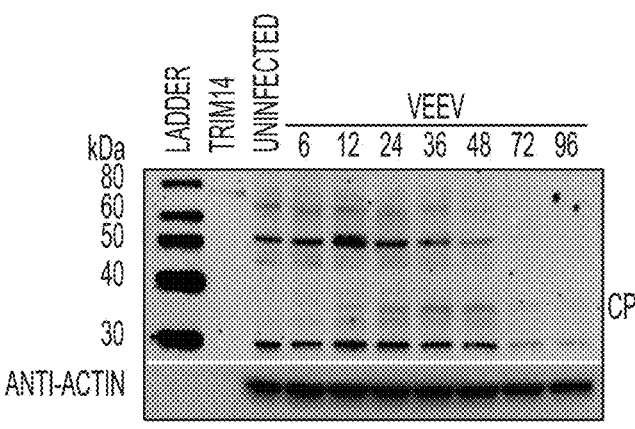
FIGS. 4A through 4E show evidence of VEEV nsP2 protease cleavage of TRIM14 in virus infected cells. Immunoblots of (FIG. 4A) VEEV, (FIG. 4B) WEEV, (FIG. 4C) EEEV-infected cell lysates probed with an anti-TRIM14 Sigma Prestige polyclonal antibody (HPA053217) that recognizes an epitope common to all 3 isoforms of TRIM14. Cell lysates were removed at various time points (6-96 h). The VEEV-infected cell lysates produced a new band with a MW consistent with VEEV nsP2 protease cleavage. Some evidence of TRIM14 cleavage was also observed in the WEEV infected cells and minor cleavage was observed in the EEEV infected cells; the recombinant forms of these two proteases did not show significant amounts of cleavage of the CFP-TRIM14-YFP substrate [SEQ ID NO: 4] in the in vitro conditions after 24 hours, while the recombinant VEEV nsP2 protease [SEQ ID NO: 25] readily cut CFP-TRIM14-YFP. The cleavage product (CP) band was not detectable in uninfected controls. Multiple bands were observed likely due to the poly-ubiquitination of TRIM14 and the multiple isoforms (α and β) of the protein.
Figure 4B:
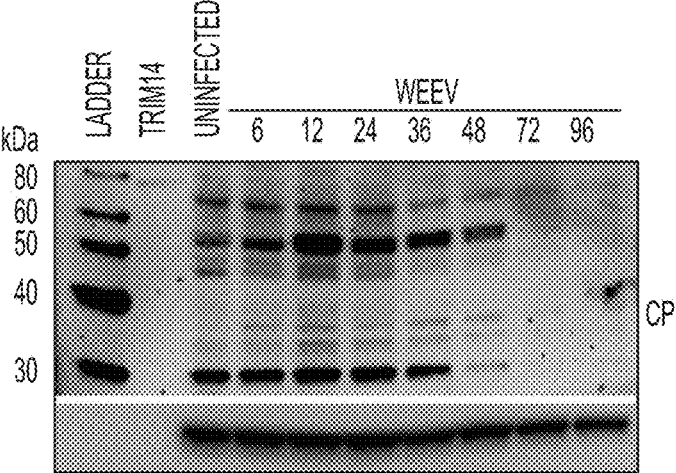
Figure 4C:
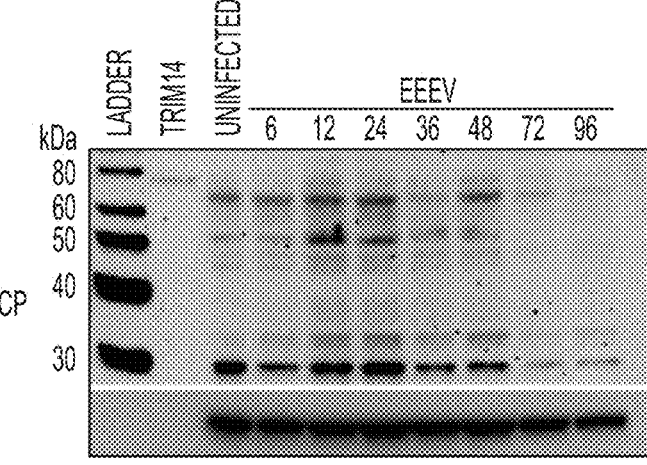

Sequence alignment analysis showed that full length TRIM14 (442 amino acids, 49.8 kDa) and the TRIM14-a isoform (406 amino acids, 45.1 kDa) contain the cleavage site while the TRIM14-β isoform (28.3 kDa) does not. TRIM14 was shown to be poly-ubiquitinated at K48 and K63 (32), and multiple bands were detected in immunoblots (FIGS. 4A, 4B, 4C). The anti-TRIM14 antibody used in this work is a Sigma Prestige™ antibody (HPA053217) (rabbit polyclonal antibody that targets human TRIM14 protein) that has been previously validated and shown to be specific for its antigen in cell lysates and peptide libraries; characterization of this antibody can be found in the Human Protein Atlas (38).

Figures 4D, 4E:
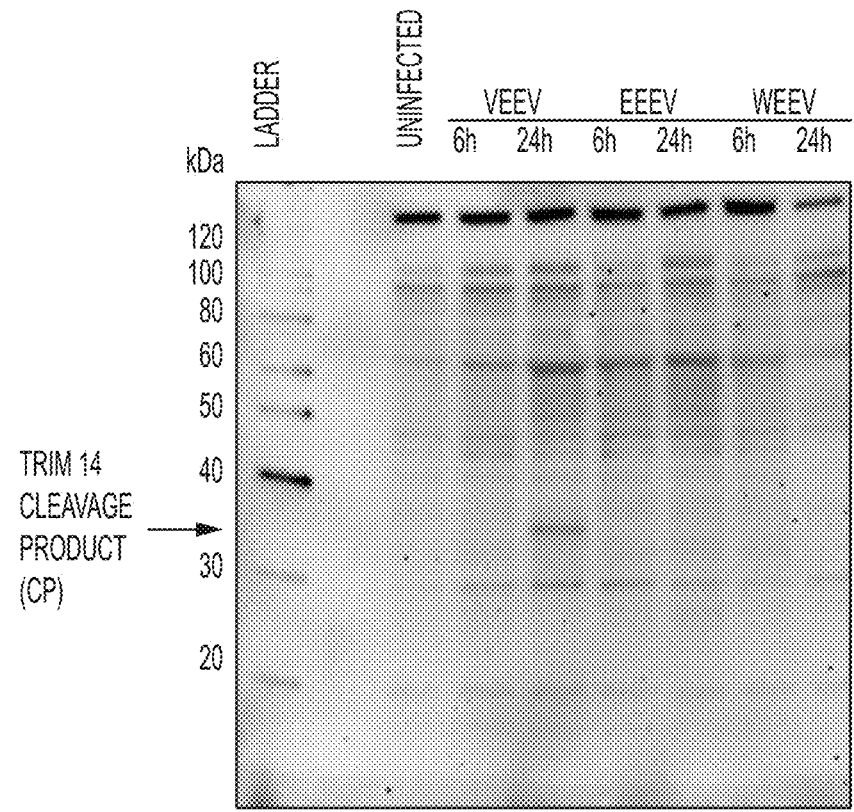

The calculated molecular weights of unmodified TRIM14 cleavage products are 37.2 kDa and 12.6 kDa (or 7.9 for the TRIM14α isoform) (FIG. 4E). The recombinant TRIM14 used as a control in the immunoblots is a GST-fusion protein (~76 kDa). It is important to note that the stability of the cleavage products in cells is unknown, and quantitative conclusions are limited using cell lysates (e.g. calculation of the percentage of TRIM14 cleaved in virus infected cells). TRIM14 is polyubiquitinated at K48 for degradation (39) and at K63 to facilitate its role in signaling (32). Overexpression of TRIM14 has been shown to suppress alphaviral replication (33) and hepatitis C replication (40.

TRIM14 cleavage in VEEV-infected cells was monitored over time, and cell lysates were collected at 6, 12, 24, 36, 48, 72, and 96 hours. The band intensities varied over time; however, only the VEEV- and WEEV-infected cell lysates contained a new ~37 kDa cleavage product that was not found in the uninfected controls (FIGS. 4A and 4B). In EEEV-infected cells, the cleavage product band was more faint (FIG. 4C). A 50 kDa band intensified during infection and may be due to enhanced expression of the TRIM14 during viral infection or release from a larger complex. The MW of the cleavage product was consistent with the calculated MW (FIG. 4E) and with the in vitro results (FIG. 2B) using purified recombinant nsP2 proteases and the 25-, 22-, and 19-residue CFP-YFP TRIM14 substrates. The result also suggests that TRIM14 can be cleaved prior to ubiquitination since the cleavage product corresponds to the MW of the non-ubiquitinated protein.

Figure 5:
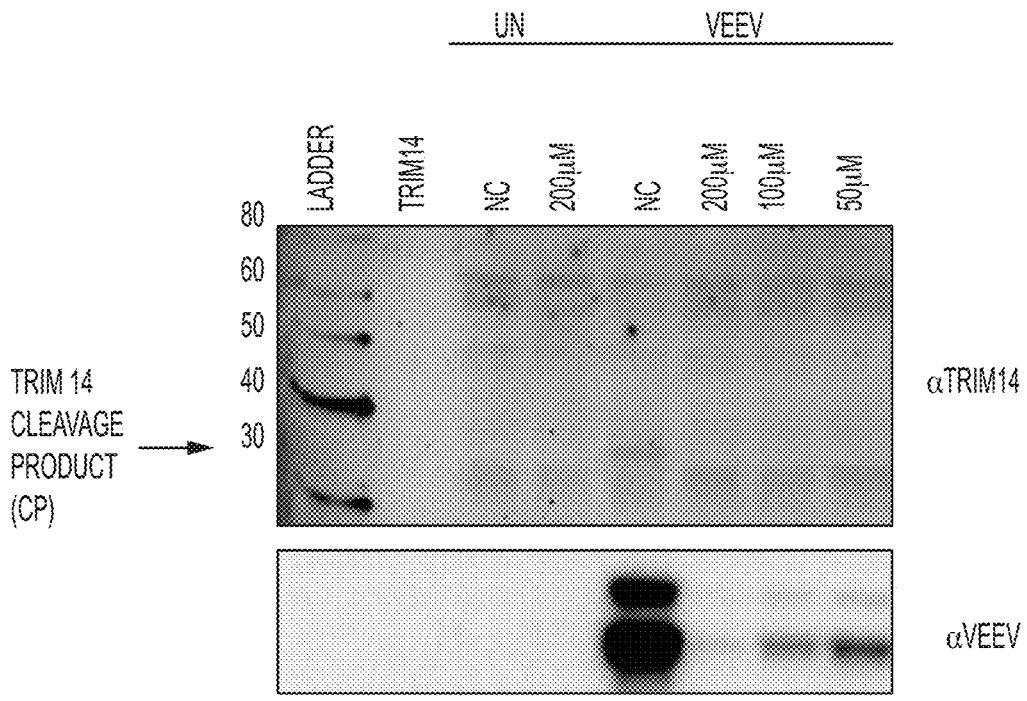
FIG. 5 shows the inhibition of VEEV nsP2 protease cleavage of TRIM14 by CA074 methyl ester. A549 cells were treated with varying concentrations of a nsP2 cysteine protease inhibitor, CA074 methylester (42), and then infected with VEEV. Cell lysates were examined by immunoblot and the blots were probed with an anti-TRIM14 antibody HPA053217. The TRIM14 CP was present in the infected cells that had not been treated with the protease inhibitor (labeled NC for "no compound"), and was absent in cell lysates treated with the nsP2 cysteine protease inhibitor. Infection was confirmed by immunoblot analysis using anti-VEEV sera in the lower blot. In the lower panel are the results of plaque assays. In the absence of the protease inhibitor, titers are ~$10^9$ plaque forming units (PFU/mL). Titers decreased significantly after treatment with CA074 methyl ester.
Figure 5:
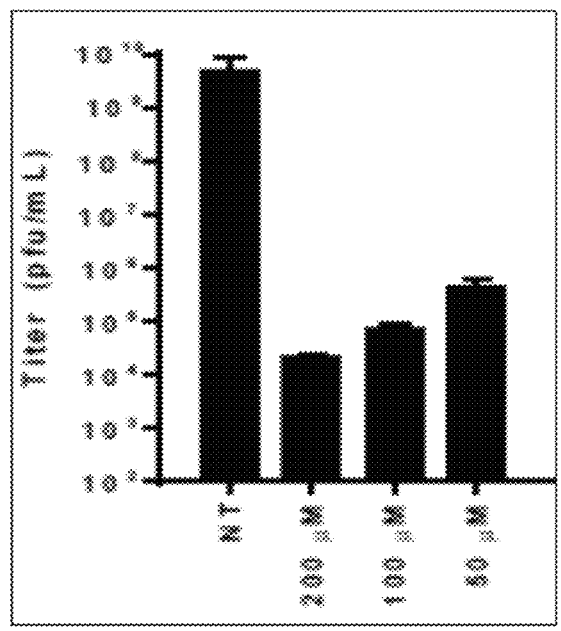

CA074 methyl ester (CA074me) was previously shown to inhibit the alphaviral VEEV nsP2 cysteine protease (42). CA074me is a Cathepsin B inhibitor; however, no other host enzymes have been shown to cleave the nonstructural polyprotein (37). CA074 is a peptide-like irreversible covalent inhibitor that specifically reacts with the nucleophilic Cys of the proteases. CA074me is the membrane permeable form of the inhibitor (prodrug). CA074me was added to cells that were infected with VEEV, and cell lysates were collected and subjected to immunoblotting. The TRIM14 cleavage product was no longer present in the CA074me-treated cells consistent with inhibition of the VEEV nsP2 cysteine protease (FIG. 5).

TRIM14 expression can be detected in the absence of virus (32) indicating that this protein is an intrinsic immune response effector protein. TRIM14 expression can also be further induced by IFNs and can also be considered as an innate immune response effector (41). Upon viral infection Lys-63-linked polyubiquitination of TRIM14 at Lys-365 occurs and was shown to be important for the assembly of the MAVS signalosome (32). Thus, cleavage of the unmodified TRIM14 may interfere with the assembly of the MAVS signalosome (FIG. 6).

For acute viral infections, species-specific anti-viral enzymes and proteins that interfere with and counteract viral replication (sometimes referred to as viral restriction factors) exist. One domain within TRIM14 appears to be important to its anti-viral functions and may account for species-specific anti-alphaviral responses (40. Human VEEV infections rarely result in lethal encephalitis (~1% of infected humans), whereas mortality rates in equine are significantly higher (e.g., EEEV's mortality rate can be as high as 90%) suggesting an inherent difference between the innate immune responses of equid vs. humans. Comparison of TRIM14 homologues from various species showed strong conservation of the full length TRIM14 sequence in humans, monkeys, rodents, pigs, cows, and chickens. The C-terminal region of equine TRIM14 is notably different, indicating that equines may harbor a different TRIM14 homologue or isoforms. The C-terminal region of TRIM14 that is cut by the viral protease was predicted to form a PRY/SPRY domain. The VEEV nsP2 cysteine protease cleavage site is within this predicted domain. The SPRY domain is a β-stranded protein interaction module commonly found in human proteins that regulate innate and adaptive immunity (43); the PRY motif consists of 3 additional β-strands N-terminal to the SPRY domain. PRY/SPRY domains contain hypervariable loop regions and a conserved core similar to a variable domain of an antibody (44). The binding specificity of the SPRY domain determines the function of the TRIM protein, and mutations within this domain have been associated with disease susceptibility (44). This domain appears to be important for mounting an effective immune response against alphaviruses, as well as HCV (40). The transient proteolytic cleavage of the PRY/SPRY domain during infection, or a difference in this domain as in the case of equine TRIM14, may impair a species' ability to mount an effective antiviral immune response to alphaviruses.

PRY/SPRY domains can be identified by 3 highly conserved sequence motifs ("LDP", "WEVD/E", "LDYE/D"). These three motifs are present in the human TRIM14 homologue, but are absent from some of the equine TRIM14 homologues. Interestingly, the donkey homologue contains the "LDYE" motif, but lacks the other two motifs. The presence or absence of the PRY/SPRY domain of TRIM14 was not sufficient to predict the virulence or pathogenicity of VEEV in other species; e.g., VEEV infections can be lethal in mice and the murine TRIM14 contains the PRY/SPRY domain. The role of TRIM14 and the downstream effectors (e.g, IFN-stimulated genes, ISG) of this pathway have not been examined across species and may differ. Species-specific differences in the Jak/STAT pathway, a pathway triggered by type I IFN, also cannot be excluded.

The PRY/SPRY domain is thought to mediate the association of TRIM14 to the C-terminal domain (residues 360-540) of MAVS (32) (FIG. 6). TRIM14 undergoes ubiquitination at a site within the PRY/SPRY domain at Lys-365 and recruits NF-κB essential modulator (NEMO) to activate the IFN regulatory factors 3 and 7 (IRF-3/7) and NF-κB pathways (32). The ubiquitination of Lys-365 was shown to be critical for the association of NEMO to the MAVS signalosome by Zhou et al. (FIG. 6). Phosphorylation of IRF-3 leads to the production of type I IFNs. The VEEV nsP2 cysteine protease cleavage site is 31 residues before Lys-365, and cleavage likely short circuits this cascade to prevent the downstream effects.

Example 2: Monitoring the Cleavage of Human Sequences by the SARS-CoV-2 Papain-Like Protease In Vitro The vast majority of host proteins cleaved by Group IV viral proteases have been shown to be involved in generating the innate immune responses (94). The cleavage of host proteins by viral proteases is a type of transient post-translational or co-translational silencing (FIG. 8).

A novel bioinformatic method developed by the inventors revealed other potential host substrates in humans (FIG. 8A). Details are provided in reference 95, incorporated herein by reference for the purposes of teaching these bioinformatics techniques. Predicted viral protease cleavage sites could be found in host proteins involved in generating the innate immune responses, but also in human proteins which have not been previously shown to be involved in generating the innate immune responses. These proteins appear to have relationships to the observed virus-induced phenotypes (symptoms). For the SARS-CoV-2 Papain-like Protease (PLpro), the highest predicted human protein substrates were the following: cardiac myosins MYH7 and MYH6, Protein S (PROS1), ErbB4 (HER4), and FOXP3. Cyan and yellow fluorescent protein (CFP/YFP) FRET substrates were made to test the cleavage of each sequence [SEQ ID NOs: 7, 8, 9, 10, 11, 12] by the PLpro enzymes. Cleavage of these substrates by the SARS-CoV-2 PLpro [SEQ ID NO: 26] was predicted (FIG. 8A) and observed in vitro (FIG. 8B). The substrates were subjected to both the SARS-CoV-2 and MERS PLpro enzymes for 21-96 h at room temperature. SEQ ID NOs: 7, 8, 9, 11, 12 were cleaved by the SARS-CoV-2 and MERS PLpro enzymes [SEQ ID NOs: 26 and 27], while SEQ ID NO: 10 was only cleaved by the SARS-CoV-2 PLpro. The most readily cleaved substrates by the SARS-CoV-2 PLpro were SEQ ID NOs: 7 and 8 which correspond to a sequence found in MYH6 and MYH7 (FIG. 8B). A MERS C112A PLpro variant was used as a control (95).

Bovine heart lysates made from the left ventricle (LV) were then treated with the SARS-CoV-2 and MERS PLpro enzymes [SEQ ID NOs: 26, 27] and cleavage of MYH6 was detected in immunoblots probed with an anti-MYH6 antibody (FIG. 8C). A new lower molecular weight band appeared after treatment of the heart lysates with the PLpro at room temperature indicating that the full length protein could be similarly cut. The cleavage site lies within a helix breaking sequence. Mass spectrometry was used to confirm the cleavage site of the FRET substrate by the SARS-CoV-2 PLpro (not shown).

Recombinant FOXP3 protein (1-260 amino acids) was also shown to be cut by the SARS-CoV-2 and MERS PLpro enzymes. The cleavage site was N-terminal to the DNA binding domain and the scissile bond was confirmed by mass spectrometry. FOXP3 is a key transcription factor in Treg cells, the cells that tamp down immune responses at the end of an infection to prevent damage of tissues. ErbB4 (HER4) and the anti-coagulation protein Protein S (PROS1) were also cut. Knockout of ErbB4 in mice produces a phenotype similar to bronchopulmonary dysplasia. Deficiencies of PROS1 lead to a variety of blood clots (e.g. pulmonary embolisms, strokes, deep vein thrombosis). Heart failure, excessive lung inflammation and blood clots were observed in COVID-19 infections.

Example 3: Monitoring the Cleavage of Human Sequences by the ZIKV ns2B-Ns3 Protease In Vitro Human host protein substrates were predicted for the ns2B-ns3 protease of Zika virus. CFP-YFP substrates were: FOXG1, SFRP1, NT5M and Gs, alpha. In animal models, the cleavability of a host protein called STING correlated with the appearance of Dengue virus symptoms and pathology (96). Animals with uncleavable sequences showed little to no pathology. The uncleavable sequences could be made cleavable by single amino acid substitutions.

Thus, the identity of cleavable sequences [SEQ ID NO: 4, 5, 6, 7-22] may enable the production of transgenic animals carrying these sequences. The recapitulation of the disease pathology, or aspects of the pathology is necessary for testing drugs and vaccines that prevent the pathology. Virus-infected mice and rats often do not display the same pathology as seen in humans. The SFRP1 cleavage site sequence [SEQ ID NO: 21] was the same in humans and chickens; these two species develop microcephaly when infected with ZIKV. Rats and mice had a different SFRP1 sequence in this region and do not develop the microcephaly (94).

Disease severity can also differ between species. The cleavable sequences identified using the methods described herein, can be searched for in BLAST and any species carrying the cleavable sequence can be identified and tested with live virus to determine if other species can be used as animal models for the virus being examined. Badorff, et al (97) demonstrated that proteases from enteroviruses that cause cardiomyopathy can cut dystrophin and that the cleavage was linked with the cardiomyopathy. A cleavage-resistant knock-in mouse carrying a mutated dystrophin sequence had a decrease in the cardiomyopathy caused by coxsackievirus B2, linking the proteolytic cleavage of dytrophin with the cardiomyopathy (98).

Discussion

The proteolytic cleavage of components of the MAVS signalosome by viral proteases appears to be a common mechanism for innate immune response evasion by Group IV (+)ssRNA viruses (FIG. 6). Viral proteases can directly cleave host proteins that lead to IFN and ISG production. Cleavage of several of the targets facilitates the shutoff of host transcription and translation. For example the 3Cpro of viruses belonging to Picornaviridae have been shown to cleave RNA polymerase II transcription factors, TATA-binding protein (56;57), CREB (cAMP responsive element binding protein), Oct-1, p53, SL-1 TBP-associated factors (58), poly(A)-binding protein (59;60, eIF5B (61), eIF4AI (62), eIF4GI (63), TRIF (64), RIG-I (65), MDA-5 (66), MAVS (67) NF-κB (68), and NEMO (69; 70). The Hepatitis C (HCV) viral ns3/4A protease (Flaviviridae) was shown to cleave MAVS (71-74). Here we have shown that the VEEV nsP2 protease (Togaviridae) can cleave TRIM14. TRIF (TIR-domain-containing adapter inducing interferon-β) was another common target of viral proteases. The Dengue virus ns2B/ns3 protease was shown to cleave STING (stimulator of the interferon gene, also known as a MITA, mediator of IRF3 activation)(75), a protein that can interact with RIG-I and MAVS, but not with MDA-5. Cleavage of STING led to the inhibition of type I IFN production (75-77). Zika is another notable member of Group IV and one host protein, Septin-2, that is cleaved by its viral protease has been reported (101).

The characteristic cleavage products of viral proteases may also produce valuable biomarkers of viral infection and could be useful in the evaluation of the therapeutic efficacy of antiviral protease inhibitors in vivo. For example, MAVS cleavage products were observed in humans with chronic HCV infections, but not in controls, and the cleavage of MAVS by the HCV ns3-4A protease was associated with higher viral loads (73). Since biomarkers for alphaviral infections are relatively uncharacterized, the cleavage of TRIM14 or the downstream effects of cleavage, or both, may be useful indicators of VEEV infection. In SARS-CoV-2 infected cardiomyocytes, the cleavage of sarcomeres is evident and consistent with the cleavage of the cardiac myosins and other predicted sarcomeric proteins (99). Reductions in PROS1 were also observed in 3 studies on humans infected with SARS-CoV-2 (95).

Figure 7:
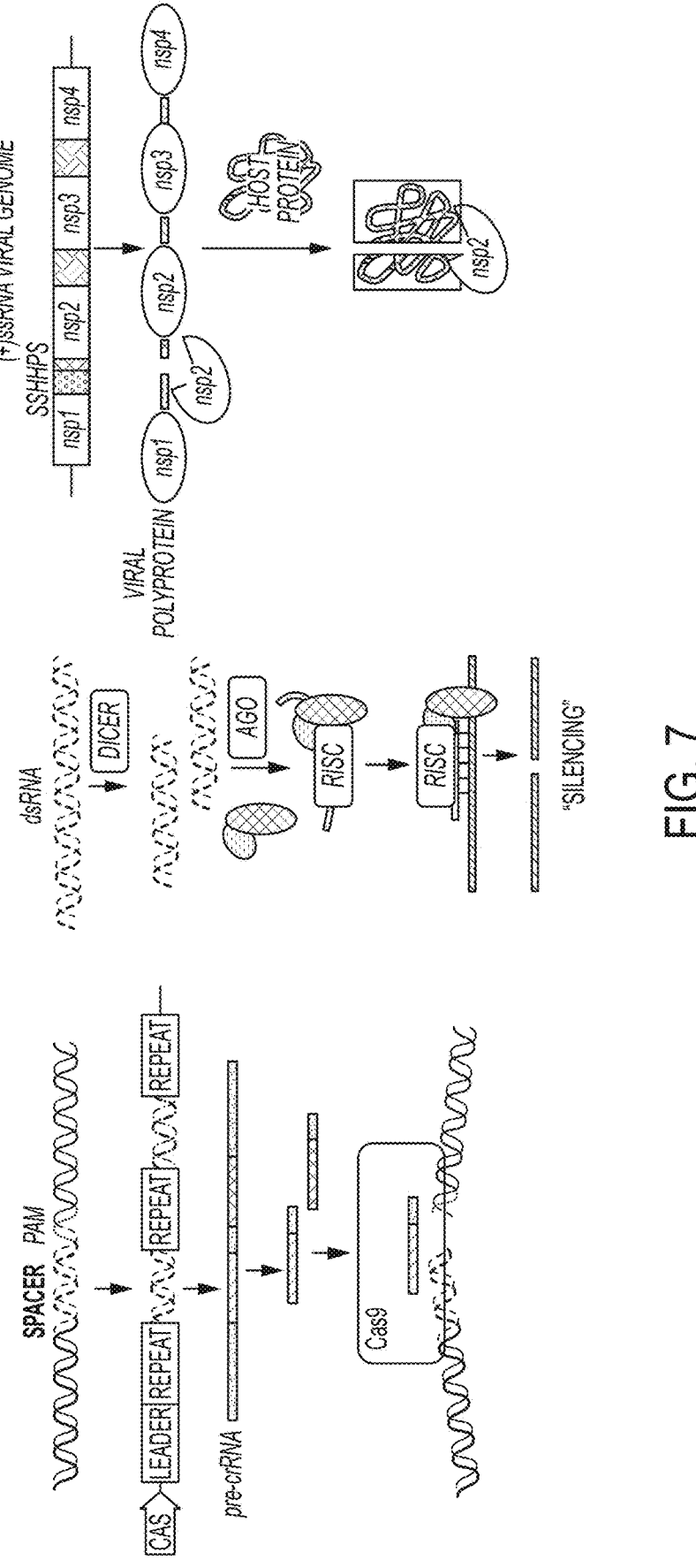
FIG. 7 illustrates three mechanisms of silencing (based on DNA, RNA, and protein) that are guided by a short sequence. In each case a short sequence is used to identify a larger target sequence for sequence-specific cleavage; these mechanisms are analogous to search and delete programs that utilize a keyword and have been written in three different languages. Each system has an enzyme that recognizes the match between the short sequence and the target, and then cuts the larger target sequence. The goal of these mechanisms is to antagonize or silence the effects of the molecule in a sequence-specific manner. These mechanisms are used to defend the host from viruses, or to defend a virus from a host's immune system. The CRISPR/Cas9 and RNAi figures have been adapted from ref. (92) and ref. (93).

The cleavage of human host proteins by viral proteases has been previously recognized by others (56;65;66;69;78-83) and may reflect a general antagonistic strategy akin to CRISPR/Cas9 and RNAi/RISC (FIG. 7). The cleavage site sequences recognized by viral proteases do not appear to be randomly selected. Several groups have shown that viral proteases can cleave host proteins at sites with relatively little sequence identity to the protease cleavage site sequence in the viral polyprotein. The cases presented here shows the longest continuous stretches of identical or similar residues shared between the viral polyprotein sequence and the host substrates. The use of this mechanism by Group IV (+)ssRNA viruses may be due to the early translation of the viral genome which is essentially a messenger RNA. The production of viral enzymes, including the RNA-dependent RNA polymerase, precedes the production of dsRNA intermediates. Thus, these viral proteases may have an opportunity to short circuit the MAVS signalosome before the intracellular antiviral responses are triggered by the dsRNA replication intermediates.

A protein version of CRISPR/Cas9 and RNAi/RISC has not been previously described, but could rely on short stretches of homologous host-pathogen protein sequences (SSHHPS) and a protease that cleaves them (FIG. 7). The relatively short viral protease cleavage sites (~25 residues) may arise from recombination events or mutations. Their similarity to antiviral intracellular host proteins may enable the virus to effectively gain a function without incorporating a significant amount of new genomic material. The strategy used by these viruses embeds another mechanism of IFN-antagonism reliant on the enzymatic activity of the viral protease (an enzyme that is typically essential for viral replication). Since viruses co-evolve with their hosts, the use of these host protein sequences in the nonstructural protein cleavage sites may have been evolutionarily advantageous since viral replication hinges on the protease. Better suppression of the host's innate immune responses would favor viral replication and could increase the fitness of the virus.

What is common among these three mechanisms of silencing is that they each rely on a short sequence to identify a larger target sequence to destroy; they are analogous to search and delete algorithms that utilize a "keyword" to identify a file to delete (FIG. 7). Each of these programs carries an enzyme able to identify a match between the short sequence and the larger sequence and then cleave the identified target. All of the mechanisms are used to silence or antagonize a response, and the relationship between the short sequence and the target sequence is typically between a host and pathogen, more specifically a virus. Last, these mechanisms are used as defense mechanisms and protect the host from viruses, or a virus from a host. In each case the "keywords," or an enzyme able to generate a short sequence (e.g. Dicer), were found with the enzyme responsible for cleavage of the target sequence.

Materials and Methods

Materials. RIPA buffer, Halt™ Protease Inhibitor Cocktail (100× solution of six protease inhibitors that prevents proteolytic degradation) and all general chemicals were purchased from Fisher Scientific (Waltham, MA). Plasmid constructs were synthesized by Genscript USA, Inc. (Piscataway, NJ). BugBuster™ (gentle disruptor of *E. coli* cell wall) and IPTG (420291) (inducer of β-D-galactosidase) were purchased from EMD Millipore (Billerica, MA). Column resins and PD-10 gel filtration columns were purchased from G. E. Healthcare (Marlborough, MA). EDTA-free Protease inhibitor tablets were from Roche, Inc. Black half-area Corning 3993 non-binding surface 96-well plates were from Corning Inc. (Corning, NY). SDS-PAGE acrylamide gels (8-16% gradient) and running buffers were from Thermo Scientific (Rockford, IL) or Abcam (Waltham, MA). The anti-TRIM14 antibody (HPA053217), the anti-actin antibody (A1978) and secondary HRP-conjugated antibodies were from Sigma (St. Louis, MO). The anti-MYH7 mouse mAb primary antibody (ab11083) and anti-MYH6

(ab207926) were from Abcam Inc. (Waltham, MA). Anti-β-actin C4 antibody (MAB1501R) was from Millipore, Inc. (Burlington, MA).

Bioinformatics. PHI-BLAST was used to search the human proteome. The viral protease cleavage sites from the polyprotein were identified based upon sequence similarity to a known cleavage site for a related virus. The ~15-25 amino acid stretch was used in PHI-BLAST (searcher of protein sequences using a combination of pattern matching and local alignment) with a short pattern of ~4 amino acids derived from the cleavage sites in the viral polyprotein. The pattern typically contains P1 and P1'. This pattern sequence limits the number of proteins in the output to those that are most likely to be substrates. The PHI-BLAST output files contain the percent identity, percent positives, alignment length, bit score, and other parameters. These numerical values were plotted. The graphs showing the alignment length vs. percent positives show a trend (FIGS. 8A and 9A). A distribution could be extracted from this graph. The host proteins that were most likely to be cut by the viral protease had the highest percent positives and alignment length. These sequences were inserted into CFP/YFP substrates and tested for cleavage.

Plasmid Constructs of FRET Substrates. A pET-15b plasmid (Ampicillin$^R$) encoding cyan fluorescent protein (CFP), an nsP viral protease cleavage site motif (e.g. AG(A/C)↓ (G/Y/A)) and yellow fluorescent protein (YFP) in between the NdeI and XhoI cut sites were synthesized. An N-terminal hexa-histidine tag preceded a thrombin cleavage site. Six CFP-YFP constructs were used for the alphaviral substrates: V12 which contains 25-residues of the VEEV nsP12 cleavage site [SEQ ID NO: 2]; V34 which contains 25-residues of the VEEV nsP34 cleavage site [SEQ ID NO: 3]; S12 which contains 25-residues of the SFV nsP12 cleavage site [SEQ ID NO: 17]; and ones containing 25-, 22-, or 19-residues of human TRIM14 [SEQ ID NO: 4, 5, 6]. Similar constructs were made for the coronaviral substrates [SEQ ID NO: 7, 8, 9, 10, 11, 12] and Zika substrates [SEQ ID NO: 19, 20, 21, 22] and uncleavable controls [SEQ ID NO: 23, 24].

The nsP2 cysteine protease-SAM MTase of CHIKV in a modified pMCSG9 vector (84) was provided by Dr. Jonah Cheung at the New York Structural Biology Center. The CHIKV protease/SAM MTase were fused to a decahistidine-tagged maltose-binding-protein at the N-terminus that could be cleaved using TEV protease. The pet15 plasmid encoding the ZIKV ns2B/ns3 protease was provided by Dr. Rolf Hilgenfeld and Dr. Jian Lei at Univ. Lübeck, Germany. Constructs of the CoV papain-like proteases were provided by Dr. Scott Pegan at University of Georgia.

Expression & Purcation of the nsP2 Cysteine Proteases. To ensure purification of the reduced state of the VEEV nsP2 cysteine protease (85), we used an nsP2-thioredoxin (Trx) fusion protein containing the protease and SAM MTase domains (residues 457-792). The EEEV and WEEV nsP2 cysteine proteases were expressed and purified using a similar protocol with an additional Q-Sepharose column purification step prior to the SP-Sepharose column. BL-21 (DE3) pLysS *E. coli* were transformed with the Trx-VEEV-nsP2 plasmid. Luria Bertani (LB) media (3-6 L) containing 50 μg/mL ampicillin and 25 μg/mL chloramphenicol was inoculated and grown to an $OD_{600}$ of approximately 1.0 and induced with 0.5 mM IPTG overnight at 17° C. Cells were pelleted and lysed with lysis buffer (50 mM Tris pH 7.6, 500 mM NaCl, 35% BugBuster, 5% glycerol, 2 mM β-mercaptoethanol (BME), 25 U of DNase 0.3 mg/mL lysozyme) and sonicated ten times for 15 second intervals in an ice bath. Lysates were clarified by centrifugation at 20,000×g for 30 minutes and loaded onto a nickel column equilibrated with 50 mM Tris pH 7.6, 500 mM NaCl, 2 mM BME, 5% glycerol. The column was washed with the same buffer containing 60 mM imidazole. Protein was eluted using the same buffer containing 300 mM imidazole. Protein was dialyzed with thrombin (overnight at 4° C.) against 50 mM Tris pH 7.6, 250 mM NaCl, 5 mM DTT, 1 mM EDTA, 5% glycerol, and then diluted 1:3 with Buffer A (50 mM Tris pH 7.6, 5% glycerol, 5 mM DTT) and loaded onto an SP-Sepharose column equilibrated with Buffer A. Protein was eluted using a salt gradient (0-1.25 M NaCl) and then concentrated, flash frozen in liquid nitrogen, and stored at −80° C. or stored at −20° C. in buffer containing 50% glycerol. The buffer was exchanged to the corresponding assay buffer (50 mM HEPES pH 7.0) prior to all kinetic experiments using PD-10 columns. The CHIKV nsP2 protease was expressed from a construct produced by Chung et al. (86) and was purified using a similar method; the His-tag and MBP were removed. The ZIKV and CoV viral proteases were purified using similar methods.

Expression & Purcation of FRET Protein Substrates. BL-21(DE3) *E. coli* were transformed with the plasmids encoding the substrates. LB/Amp (1.5 to 3.0 L) was inoculated and grown to an $OD_{600}$ of approximately 1.0 and induced with 0.5 mM IPTG overnight with shaking at 17° C.

Cells were pelleted by centrifugation, lysed with lysis buffer (50 mM Tris pH 7.6, 500 mM NaCl, 35% BugBuster, 2 mM BME, 0.3 mg/mL lysozyme, 1 EDTA-free protease inhibitor tablet), and briefly sonicated for 1 minute in an ice bath. Lysates were clarified by centrifugation (20,500×g for 30 minutes at 4° C.) and loaded onto a nickel column equilibrated with 50 mM Tris pH 7.6, 500 mM NaCl, 2 mM BME. The column was washed with the same buffer after loading and with 10-20 column volumes of buffer containing 60 mM imidazole until the A280 returned to baseline. The protein was eluted with the same buffer containing 300 mM imidazole. The protein was dialyzed against 50 mM Tris pH 7.6, 150 mM NaCl overnight at 4° C. with 50 U thrombin. The His-tag was removed by re-running the protein on a nickel column and collecting the flow-through. The protein was then dialyzed against 50 mM Tris pH 7.6, 5 mM EDTA, 250 mM NaCl (overnight at 4° C.), followed by dialysis against 50 mM Tris pH 7.6 (2 hours). Protein was loaded onto a Q-Sepharose column equilibrated with 50 mM Tris pH 7.6 and eluted with a salt gradient (0 to 1 M NaCl). All substrates were produced in high yield (typical yields were 60-80 mg per liter of media) and could be readily concentrated to 9.0-10.5 mg/mL. The substrates were used for continuous and discontinuous assays. Similar substrates have been used to study other proteases (87;88).

TABLE 2

| Substrate | Sequence | Length | Proteases cutting the substrate |
|---|---|---|---|
| CFP-MYH6/7-YFP | EAEQIALKGG↓KKQLQK (SEQ ID NO: 7) | 16 | SARS-CoV-2, MERS PLpro |
| CFP-MYH6/7-YFP | GGPHRLDEAEQIALKGG↓KKQLQK (SEQ ID NO: 8) | 23 | SARS-CoV-2, MERS PLpro |
| CFP-PROS1-YFP | IYHSAWLLIALPGG↓KIEVQL (SEQ ID NO: 9) | 20 | SARS-CoV-2, MERS PLpro |
| CFP-ErbB4(HER4)-YFP | LKNLTRILNGG↓VYVDQ (SEQ ID NO: 10) | 16 | SARS-CoV-2 PLpro |
| CFP-FOXP3-YFP | GGTFQGPDLRGG↓AHASSS (SEQ ID NO: 11) | 18 | SARS-CoV-2, MERS PLpro |
| CFP-FOXP3-YFP | LLSARGPGGTFQGRDLPGG↓AHASSS (SEQ ID NO: 12) | 25 | SARS-CoV-2, MERS PLpro |
| CFP-TRIM14-YFP | RHYWEVDVQEAGA↓GWWVGA (SEQ ID NO: 13) | 19 | VEEV nsP2 cysteine protease |
| CFP-TRIM14-YFP | ATGRHYWEVDVQEAGA↓GWWVGA (SEQ ID NO: 14) | 22 | VEEV nsP2 cysteine protease |
| CFP-TRIM14-YFP | DCFATGRHYWEVDVQEAGA↓GWWVGA (SEQ ID NO: 15) | 25 | VEEV nsP2 cysteine protease |
| CFP-SFVp12-YFP 11:6 | DVEELEYHAGA↓GVVETP (SEQ ID NO: 16) | 17 | CHIKV and VEEV nsP2 cysteine protease |
| CFP-SFVp12-YFP 19:6 | AETGVVDVDVEELEYHAGA↓GVVETP SEQ ID NO: 17) | 25 | CHIKV and VEEV nsP2 cysteine protease |
| CFP-VEEV nsP12-YFP | VEEPTLEADVDLMLQEAGA↓GSVETP (SEQ ID NO: 2) | 25 | VEEV nsP2 cysteine protease |
| CFP-VEEVnsP23-YFP | LSSTLTNIYTGSRLHEAGC↓APSYHV (SEQ ID NO: 18) | 25 | VEEV nsP2 cysteine protease |
| CFP-VEEVnsP34-YFP | TREEFEAFVAQQQRFDAGA↓YIFSSD (SEQ ID NO: 3) | 25 | VEEV nsP2 cysteine protease |
| CFP-SFRP1-YFP | MGIGRSEGGRR↓GAALGVLLALGAAL (SEQ ID NO: 19) | 25 | ZIKV ns2B-ns3 protease |

TABLE 2-continued

CFP-YFP substrates

| Substrate | Sequence | Length | Proteases cutting the substrate |
|---|---|---|---|
| CFP-GsGTPalpha-YFP | PVRSSAPRRGHSVASAPRSGLRQVAGRR↓GAALPCS (SEQ ID NO: 20) | 35 | ZIKV ns2B-ns3 protease |
| CFP-NT5M-YFP | MIRLGGWCARRLCSAAVPAGRR↓GAAGGLGLAGGR (SEQ ID NO: 21) | 34 | ZIKV ns2B-ns3 protease |
| CFP-FOXG1-YFP | RSTTSRAKLAFKR↓GARLTSTG (SEQ ID NO: 22) | 21 | ZIKV ns2B-ns3 protease |
| CFP-SFRP2-YFP | MLQGPGSLLLLFLASHCCLGSARGLFLFGQPDFS (SEQ ID NO: 23) | 34 | Control, not cleaved by ZIKV ns2B-ns3 protease |
| CFP-SFRP4-YFP | MFLSILVALCLWLHLALGVRGAPCEAVRIPMCRH (SEQ ID NO: 24) | 34 | Control, not cleaved by ZIKV ns2B-ns3 protease |

In the practical examples described herein, the sequences in Table 2 above were typically used with a cyan fluorescent protein (CFP) and yellow fluorescent protein (YFP) at their N-terminus and C-terminus, respectively. However, one could use alternative fluorophores to facilitate detection of substrate cleavage, preferably a FRET pair of fluorophores. Moreover, one could use the substrates without fluorophores and instead detect cleavage by other means, such as immunohistochemistry (IHC), enzyme linked-immunosorbent assay (ELISA), SDS-PAGE, mass spectrometry, and/or flow cytometry.

Continuous FRET Assay. For measurement of steady state kinetic parameters the method described by Ruge et al. was followed (88). Cleavage of the YFP/CFP FRET substrates was monitored continuously at room temperature ($23\pm3°$ C.) using excitation/emission wavelengths of 434/470 nm and 434/527 nm to calculate emission ratios and a SpectraMax M5 plate reader from Molecular Devices. The substrate was buffer-exchanged into 50 mM HEPES pH 7.0. Enzyme concentrations of $\leq 1$ $\mu$M and a substrate concentration range of 10-140 $\mu$M (8 different concentrations) were used to measure Steady State kinetic parameters. Data were col-

TABLE 3

Recombinant Proteases

| Protease | Sequence | Length |
|---|---|---|
| Recombinant VEEV nsP2-thioredoxin Protease containing residues 457-792 | MSDKIIHLTDDSFDTDVLKADGAILVDFWAEWCGPCKMIAPILDEIADEYQGKLTVAKLNI DQNPGTAPKYGIRGIPTLLLFKNGEVAATKVGALSKGQLKEFLDANLAGSGSGHMHHHHHH SSGLVPR*GSMRHILERPDPTDVFQNKANVCWAKALVPVLKTAGIDMTTEQWNTVDYFETD KAHSAEIVLNQLCVRFFGLDLDSGLFSAPTVPLSIRNNHWDNSPSPNMYGLNKEVVRQLSR RYPQLPRAVATGRVYDMNTGTLRNYDPRINLVPVNRRLPHALVLHHNEHPQSDFSSFVSKL KGRTVLVVGEKLSVPGKMVDWLSDRPEATFRARLDLGIPGDVPKYDIIFVNVRTPYKYHHY QQCEDHAIKLSMLTKKACLHLNPGGTCVSIGYGYADRASESIIGAIARQFKFSRVCKPKSS LEETEVLFVFIGYDRKARTHNPYKLSSTLTNIYTGSRLHEA [SEQ ID NO: 25] | 467 |
| Recombinant SARS-CoV-2 Papain-like Protease | MGSSHHHHHHSSGLVPRGSHMEVRTIKVFTTVDNINLHTQVVDMSMTYGQQFGPTYLDGAD VTKIKPHNSHEGKTFYVLPNDDTLRVEAFEYYHTTDPSFLGRYMSALNHTKKWKYPQVNGL TSIKWADNNCYLATALLTLQQIELKFNPPALQDAYYRARAGEAANFCALILAYCNKTVGEL GDVRETMSYLFQHANLDSCKRVLNVVCKTCGQQQTTLKGVEAVMYMGTLSYEQFKKGVQIP CTCGKQATKYLVQQESPFVMMSAPPAQYELKHGTFTCASEYTGNYQCGHYKHITSKETLYC IDGALLTKSSEYKGPITDVFYKENSYTTTIK [SEQ ID NO: 26] | 336 |
| Recombinant MERS-CoV-2 Papain-like Protease | MGSSHHHHHHSSGLVPRGSHMGSSHHHHHHSSGLVPRGSQLTIEVLVTVDGVNFRTVVLNN KNTYRSQLGCVFFNGADISDTIPDEKQNGHSLYLADNLTADETKALKELYGPVDPTFLHRF YSLKAAVHGWKMVVCDKVRSLKLSDNNCYLNAVIMTLDLLKDIKEVIPALQHAFMKHKGGD STDFIALIMAYGNCTFGAPDDASRLLHTVLAKAELCCSARMVWREWCNVCGIKDVVLQGLK ACCYVGVQTVEDLRARMTYVCQCGGERHRQLVEHTTPWLLLSGTPNEKLVTTSTAPDFVAF NVFQGIETAVGHYVHARLKGGLILKFDSGTVSKTSDWKCKVTDVLFPGQKYSSDCN [SEQ ID NO: 27] | 361 |
| Recombinant ZIKV ns2B/ns3 Protease | MGSSHHHHHHSSGLVPRGSHMVDMYIERAGDITWEKDAEVTGNSPRLDVALDESGDFSLVE DDGPPMAGGGGSGGGGSGALWDVPAPKEVKKGETTDGVYRVMTRGLLGSTQVGVGVMQEGV FHTMWHVTKGSALRSGEGRLDPYWGDVKQDLVSYSGPWKLDAAWDGHSEVQLLAVPPGERA RNIQTLPGIFKTKDGDIGAVALDYPAGTSGSPILDKSGRVIGLYGNGVVIKNGSYVSAITQ GRR [SEQ ID NO: 28] | 247 |
| Recombinant CHIKV nsP2 protease | SNAFQNKANVCWAKSLVPILETAGIKLNDRQWSQIIQAFKEDKAYSPEVALNEICTRMYGV DLDSGLFSKPLVSVYYADNHWDNRPGGKMFGFNPEAASILERKYPFTKGKWNINKQICVTT RRIEDFNPTTNIIPVNRRLPHSLVAEHRPVKGERMEWLVNKINGHHVLLVSGYNLALPTKR VTWVAPLGVRGADYTYNLELGLPATLGRYDLVVINIHTPFRIHHYQQCVDHAMKLQMLGGD SLRLLKPGGSLLIRAYGYADRTSERVICVLGRKFRSSRALKPPCVTSNTEMFFLFSNFDNG RRNFTTHVMNNQLNAAFVG [SEQ ID NO: 29] | 324 | lected in triplicate (50 µL reaction volumes) in half-area black low binding surface 96-well plates from Corning, Inc. After the reads were completed the plates were sealed with film and allowed to digest overnight at room temperature 23±3° C. Final emission ratios were read the next day. The fraction of substrate cleaved, f, was calculated from the emission ratios at each time point using the following equation:

$$f = \frac{\left[\frac{\left(\frac{ex434}{em527}\right)}{\left(\frac{ex434}{em470}\right)} - r_{uncut}\right]}{(r_{cut} - r_{uncut})}$$

The nmols of substrate cleaved at each time point was calculated by multiplying f by the nmols of substrate at t=0 ($S_o$). The value of $r_{uncut}$ corresponds to the emission ratio measured in the absence of enzyme, and the value of $r_{cut}$ is the emission ratio measured when the substrate was fully cleaved. Initial velocities were calculated at each [S] concentration from the linear range (f≤20%). Plots of time vs. nmols were linearly fit for each [S] concentration, and $v_o$ was obtained from the slopes of the lines. Rates of spontaneous hydrolysis were measured in the absence of enzyme and were subtracted from the enzyme catalyzed rates. Data were fit to the Michaelis-Menten equation, $v_o=(V_{max}*[S])/(K_m+[S])$, using Grafit (Erithricus Software Ltd., Surrey, UK).

Discontinuous Gel-Based Assay. Reaction mixtures (5 µM nsP2-Trx, 50 µM FRET substrate [SEQ ID NOs: 2-24], 50 mM HEPES pH 7.0, 150 mM NaCl) were incubated overnight (~18 h) at room temperature (23±3° C.). The reactions were run until >90% of the substrate was cleaved by the enzyme. Reactions were stopped by mixing with Laemelli buffer (1:1) and heating the samples for 3 minutes at ≥70° C. Cleavage products (10 µL) were separated by SDS-PAGE in 12-well 8-16% gradient gels in BupH running buffer (100 mM Tris, 100 mM HEPES, 3 mM SDS, pH 8±0.5) at 110 V for 50 minutes. The calculated molecular weight of the uncut TRIM14 FRET substrate containing a 25 amino acid cleavage sequence was 56.7 kDa, and 29.2 kDa and 27.5 kDa for the cut CFP and YFP products, respectively. The molecular weight of the enzyme for the thioredoxin-His-tagged enzyme was 52.208 kDa, and 38.29 kDa for the Tag-free enzyme. The bands were well separated in 8-16% gradient gels, and boiling of the samples was required to achieve the sharp banding pattern. Densitometry was done using the BioRad Gel Dock Imager software (BioRad Inc., Hercules, CA).

Mass Spectrometry. Gel bands were washed with 250 mM ammonium bicarbonate in 50% acetonitrile (ACN) until completely destained. Bands were then cut into small cubes and dehydrated by 100% (ACN). Modified porcine trypsin solution (Promega, product no. V511) in 50 mM ammonium bicarbonate was added to the gel cubes, and proteins were in gel digested overnight. The resulting peptides were extracted from the gel pieces by sonication in 2% formic acid (FA) in 60% ACN. The extracts were then collected, and this step was repeated three more times. A final gel dehydration step (i.e., sonication with 100% ACN) was used to minimize peptide loss. Peptide digests corresponding to the same band were combined and concentrated via speedvac.

Concentrated in-gel digests were reconstituted in 0.1% FA and 5% ACN and injected onto a reverse phase column (C18, Michrom Magic—C18AQ-5µ 200 Å 0.1×150 mm) using a Tempo MDLC system (AB Sciex, Foster City, CA) coupled to a quadrupole-time of flight MS/MS Q-Star Elite mass spectrometer (AB Sciex). Peptides were loaded onto the column using 98% solvent A (5% ACN, 0.1% FA in water) and 2% solvent B (95% ACN, 0.1% FA in water) for 30 min and separated by a 130 min linear gradient of increasing solvent B by 0.37%/min to a final concentration of 50%. MS and MS/MS peptide spectra were acquired using information dependent acquisition (IDA). A mass range of 350-1600 Da was monitored in TOF MS scan. The three most abundant precursor ions from TOF MS scans with an intensity >20 counts per second were submitted for MS/MS analyses. Former target ions were excluded from MS/MS submission for 15 s. MS data were acquired using Analyst QS (AB Sciex), and tandem mass spectra were extracted by mascot.dll and analyzed using Mascot (Matrix Science, London, UK; Mascot Server version 2.4.1). Mascot was set up to search three in house databases: 1: contaminants 20120713 (247 sequences; 128,130 residues), 2: cRAP 20121128 (112 sequences; 37,418 residues), and 3: VEEV database (6 sequences; 1,980 residues). Common contaminants were included in the first two databases while the complete VEEV protease, thioredoxin, complete sequence of CFP-TRIM14-YFP, as well as its predicted N-terminal and C-terminal sequences as produced by VEEV. Assuming the digestion was semitryptic (at least one peptide terminal was R or K) and allowing for 3 miscleavages. Fragment ion mass tolerance was set to 0.20 Da and a parent ion tolerance to 0.20 Da. Deamidation of asparagine and glutamine, oxidation of methionine were set as variable modifications. After identification by Mascot, the spectra of resulting N-terminal and C-terminal peptides of CFP-TRIM14-YFP [SEQ ID NO: 4] products from VEEV proteolysis: were inspected manually in the raw acquired data, and the resulting singly charged fragments were manually annotated. MS confirmation of CoV PLpro cleavage was also performed for [SEQ ID NOs: 8, 9, 11] (94).

Western Blotting. Cells were lysed in RIPA buffer containing Halt Protease Inhibitor Cocktail at a 2× final concentration. Lysates were separated in a 10% NuPAGE Bis-Tris gel and electroblotted onto a nitrocellulose membrane using the iBlot system (Invitrogen). Following protein transfer, blots were blocked in 1×PBS containing 0.05% Tween-20 and 5% dry milk and incubated at 4° C. overnight. Protein-specific primary antibodies were diluted in blocking buffer and incubated at RT for 2 hrs. Following incubation, blots were washed 3 times with PBS containing 0.05% Tween-20 (PBST). After washing blots were incubated with corresponding secondary antibody at RT for 1 hr then washed 3 times with PBST. For protein detection, blots were treated with SuperSignal™ West Pico Chemiluminescent Substrate and imaged using BioRad imaging software. Trim14 protein was detected using a polyclonal anti-Trim14 Ab (1:500, HPA053217) followed by goat anti-rabbit Horseradish peroxidase (HRP, 1:500) secondary Ab. Actin protein was detected using anti-actin Ab (1:5000) followed by goat anti-mouse HRP (1:5000) secondary Ab. The VEEV nsP2 protein was detected using goat anti-VEEV nsP2 Ab (kind gift from AlphaVax, Research Triangle Park, NC, 1:1000) followed by rabbit anti-goat HRP (1:5000) secondary Ab.

A549 cells (adenocarcinoma human alveolar basal epithelial cells) were used. Infected A549 cell lysates collected at 6 and 24 h post-infection (10 µg/lane) were separated in a 10% NuPAGE Bis-Tris gel and transferred onto a nitrocellulose membrane. Trim14-α, Trim14-α cleavage product (CP), and α-actin were detected by Western blot analysis using protein specific antibodies. Recombinant Human Trim 14 protein was used as control. The VEEV Trinidad, EEEV FL93-939, WEEV CBA87, and CHIKV AF15561 viruses were used.

To test the effects of a previously identified VEEV nsP2 cysteine protease inhibitor (42), CA074 methylester (CA074me), A549 cells were treated with CA074me and infected at a multiplicity of infection equal to 10 with VEEV or CHIKV. After incubation of virus with cells for 1 h, cell monolayers were washed twice with medium to remove residual virus. Complete medium containing CA074me (50, 100, 200 μM) was added, and the cells were incubated at 37° C., 5% $CO_2$. At 18-24 h post-infection, supernatants and cell lysates were collected for analysis by western blot.

The specificity of the polyclonal rabbit Sigma Prestige™ anti-TRIM14 antibody (HPA053217) has already been analyzed and is available online (38). The HPA053217 antibody had been raised using an N-terminal sequence is common to full-length TRIM and the α- and β-isoforms of TRIM14. The sequence precedes the ubiquitination site Modeling of Substrate binding interaction. The binding models of substrates including VEEV P12, P23, P34 and TRIM14 were predicted with an ensemble-docking protocol using the AutoDock program (89). Multiple conformations of the VEEV nsP2 structure (PDB 2HWK) and the CHIKV nsP2 (PDB 3TRK) were obtained from MD simulations and cluster analysis. The active site of the protein was defined by a grid of 70×70×70 points with a grid spacing of 0.375 Å centered at the catalytic residue Cys-477. The Lamarckian Genetic Algorithm (LGA) was applied with 50 runs, and the best pose with the most favorable binding free energy was selected. MD simulations were performed for the predicted substrate binding models using the AMBER 12 package and the ff99SB force field. The solvated systems were subjected to a thorough energy minimization prior to MD simulations. Periodic boundary conditions were applied to simulate a continuous system. The particle mesh Ewald (PME) method was employed to calculate the long-range electrostatic interactions. The simulated system was first subjected to a gradual temperature increase from 0 K to 300 K over 100 ps, and then equilibrated for 500 ps at 300 K, followed by production runs of 2-ns length in total. The binding free energies were calculated using the MM-PBSA method. Decomposition of the calculated binding free energies was performed using the same MM-PBSA module in AMBER 12 package.

Detection and Treatment of Infection

Cleavage products of the proteases listed in Table 2 could be used diagnostically. For example, material (such as blood or tissue) from an individual could be assayed for the possible presence of a product to determine whether or not the patient might be infected with a particular virus. This can involve the detection of one or more cleavage products of any one or more of VEEV nsP2-thioredoxin protease, SARS-CoV-2 papain-like protease, MERS-CoV papain-like protease, ZIKV ns2B/ns3 protease, and CHIKV nsP2 protease, among others. Such an assay can be performed using any suitable technique, for example immunohistochemistry (IHC), enzyme linked-immunosorbent assay (ELISA), mass spectrometry, and/or flow cytometry.

At least eight other Group IV (+)ssRNA viral proteases have been shown to cleave components of the MAVS signalosome to antagonize IFN production, suggesting that the recombination or assimilation of these short cleavage site motif sequences to host protein sequences may represent an embedded mechanism of IFN antagonism. Thus, it is expected that the technique could be used to detect host-pathogen interactions during infection by other members of this viral family.

Such a technique could be incorporated into a diagnostic assay or predictive software program.

If a viral infection is detected in a patient, then that patient should be provided with a treatment suitable for the treatment. In various aspects, this could include the administration of a therapeutic antibody effective against the detected virus, and/or other suitable medicament.

Post-Translational Silencing

Also contemplated is a protein analog to CRISPR/Cas9 and RNAi/RISC. This system relies on the short stretches of homologous host-pathogen sequences (SSHHPS) and a sequence-specific protease (as opposed to a nuclease) that cleaves them.

The viral genome provides a delivery vehicle for the RNA encoding a wild type or mutated nsP2 protease directly into the cytoplasm (as opposed to endosomal vesicles). Other gene delivery methods could be used to transiently express the nsP2 protease locally, such as mRNA. The catalytic nature of the protease may allow it to turnover many substrates within a cell. Replication of mutant or wild type viruses would offer a mechanism to transiently propagate the effects. This type of proteome editing method has not been exploited previously, and has the potential for therapeutic application since specific targets of the viral proteases were identified (Tables 1, 2).

In one embodiment, a host cell or organism expresses a recombinant viral nonstructural polyprotein that incorporates the sequence acted upon by the viral nsP protease such as a transgenic animal model harboring mutation(s) that convert a host protein from an uncleavable sequence to a cleavable sequence. Introduction of the virus to the cell or organism results in cleavage of the sequence in the polyprotein and host protein which can lead to loss of function of the protein that is cleaved.

As described above, in vitro trials using CFP/YFP substrates as described above found that viral proteases can cleave specific host protein sequences (~14-25 amino acids). Cleavage sites were confirmed via mass spectrometry.

Experiments found that the endogenous TRIM14 protein in human A549 cells could be cleaved using the VEEV nsP2 protease. This process could be halted by treating the cells with the protease inhibitor CA074me. Such treatment also halted viral replication, since the virus could no longer suppress the innate immune responses. This showed that the post-translational silencing of TRIM14 by the viral protease could be controlled with the use of a protease inhibitor A further aspect involves identifying targets for proteome editing in silico. The targets have relationships to the observed symptoms caused by the virus. Computer hardware and software (including, for example, virtual machines) can be used to compare viral protease recognition sequences against a list of proteins in a host to find potential matches. Suitable software can include, for example, the pattern-hit initiated basic local alignment search tool (PHI-BLAST) and the bioinformatics methods described. Potential targets can then be tested in vitro to confirm or reject the findings made in silico.

Protease expression could be induced in any number of ways, such as by introducing mRNA to cells, introducing DNA for the development of transgenic animal models, or infection with a suitable virus. Optionally, the virus is attenuated and/or genetically modified. Recombinant forms protease could also be used to cleave extracellular proteins in some cases.

Proteases from bacterial pathogens that recognize human proteins such as botulinum neurotoxin have been utilized for a variety of clinical applications. The SARS-CoV-2 PLpro specifically cleaved a sequence within the human anticoagulation protein (Protein S, PROS1), cardiac myosins (MYH6, MYH7), FOXP3, and erbB4(HER4). The Zika virus protease cleaved sequences in human FOXG1, SFRP1, NT5M, and Gs,alpha (GAS).

In a further embodiment, a viral protease is mutated to act upon an amino acid sequence of interest (different from the homologous host-pathogen protein sequence), so that the introduction of a virus carrying the mutated protease results in proteolysis of the desired target.

Advantages and New Features

Viral proteases could be mutated or used as-is to recognize other host protein sequences to proteolytically shut-off cascades that lead to gene expression or to proteolyze a single protein. Embodiments can include introducing a wild type or modified protease into cells in vitro or in vivo (the cells including, for example, cell culture, tissue culture, and/or living animals optionally including humans) using techniques available in the art such as transfection, transgenics, infection with wild-type or genetically engineered virus, etc. Optionally, one or more genetically engineered or wild-type targets for the protease can be introduced as well. This strategy may be useful to kill tumor cells where oncogene expression has already taken place or for removing protein toxins. Other applications can include therapy to treat or prevent various disease, research into viral infection, and other situations where it can be desirable to cleave proteins within cells.

Alphaviruses can infect a variety of cell types and are pantropic. These viruses cause transient acute viral infections, and attenuated alphaviruses are currently in use for vaccination. The mutations that attenuate the TC-83 vaccine strain do not affect protease activity of the nsP2 cysteine protease. Some alphaviruses like VEEV are also able to cross the blood-brain barrier. The virion may serve as a useful delivery vehicle for RNA and for proteases to the brain.

The substrates sequences identified herein [SEQ ID NOs: 2-22] may be useful for examining competitive inhibitors. These substrates mimic proteins that are present in high concentration in certain cell types (e.g. cardiac myosins) which could interfere with inhibitor binding.

CONCLUDING REMARKS

All documents mentioned herein are hereby incorporated by reference for the purpose of disclosing and describing the particular materials and methodologies for which the document was cited.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

REFERENCES

1. Steele, K. E., Reed, D., Glass, P. J., Hart, M. K., Ludwig, G. V., Pratt, W. D., Parker, M. D., and Smith, J. F. (2007) Alphavirus Encephalitides, in Medical Aspects of Biological Warfare (Dembek, Z. F., Ed.) pp 241-270, Office of the Surgeon General, Falls Church.
2. Schafer, A., Brooke, C. B., Whitmore, A. C., and Johnston, R. E. (2011) The role of the blood-brain barrier during Venezuelan equine encephalitis virus infection, J Virol. 85, 10682-10690.
3. Ryzhikov, A. B., Tkacheva, N. V., Sergeev, A. N., and Ryabchikova, E. I. (1991) Venezuelan equine encephalitis virus propagation in the olfactory tract of normal and immunized mice, Biomed. Sci. 2, 607-614.
4. Steele, K. E. and Twenhafel, N. A. (2010) REVIEW PAPER: pathology of animal models of alphavirus encephalitis, Vet. Pathol. 47, 790-805.
5. Steele, K. E., Reed, D., Glass, P. J., Hart, M. K., Ludwig, G. V., Pratt, W. D., Parker, M. D., and Smith, J. F. (2007) Alphavirus Encephalitides, in Medical Aspects of Biological Warfare (Dembek, Z. F., Ed.) pp 241-270, Office of the Surgeon General, Falls Church.
6. Hanson, R. P., Sulkin, S. E., Beuscher, E. L., Hammon, W M., MCKINNEY, R. W, and Work, T. H. (1967) Arbovirus infections of laboratory workers. Extent of problem emphasizes the need for more effective measures to reduce hazards, Science 158, 1283-1286.
7. Ehrlich, R. and Miller, S. (1971) Effect of relative humidity and temperature on airborne Venezuelan equine encephalitis virus, Appl. Microbiol. 22, 194-199.
8. Zacks, M. A. and Paessler, S. (2010) Encephalitic alphaviruses, Vet. Microbiol. 140, 281-286.
9. Johnson, K. M. and Martin, D. H. (1974) Venezuelan equine encephalitis, Adv. Vet. Sci. Comp Med 18, 79-116.
10. Deresiewicz, R. L., Thaler, S. J., Hsu, L., and Zamani, A. A. (1997) Clinical and neuroradiographic manifestations of eastern equine encephalitis, N Engl J Med 336, 1867-1874.
11. (2009) Encyclopedia of microbiology Elsevier, New York.
12. Fields, B. N., Knipe, D. M., and Howley, P. M. (2007) Fields' virology Wolters Kluwer Health/Lippincott Williams & Wilkins, Philadelphia.
13. Yin, J., Gardner, C. L., Burke, C. W, Ryman, K. D., and Klimstra, W B. (2009) Similarities and differences in antagonism of neuron alpha/beta interferon responses by Venezuelan equine encephalitis and Sindbis alphaviruses, J Virol. 83, 10036-10047.
14. Garmashova, N., Gorchakov, R., Volkova, E., Paessler, S., Frolova, E., and Frolov, I. (2007) The Old World and New World alphaviruses use different virus-specific proteins for induction of transcriptional shutoff, J Virol. 81, 2472-2484.
15. Hahn, C. S., Lustig, S., Strauss, E. G., and Strauss, J. H. (1988) Western equine encephalitis virus is a recombinant virus, Proc Natl Acad Sci USA 85, 5997-6001.
16. Furr, M. and Reed, S. (2015) Equine Neurology Wiley, Somerset.
17. Akhrymuk, I., Frolov, I., and Frolova, E. I. (2016) Both RIG-I and MDAS detect alphavirus replication in concentration-dependent mode, Virology 487, 230-241.
18. Nikonov, A., Molder, T., Sikut, R., Kiiver, K., Mannik, A., Toots, U., Lulla, A., Lulla, V., Utt, A., Merits, A., and Ustav, M. (2013) RIG-I and MDA-5 detection of viral RNA-dependent RNA polymerase activity restricts positive-strand RNA virus replication, PLoS Pathog. 9, e1003610.

19. Kell, A. M. and Gale, M., Jr. (2015) RIG-I in RNA virus recognition, Virology 479-480, 110-121.

20. Frolova, E. I., Fayzulin, R. Z., Cook, S. H., Griffin, D. E., Rice, C. M., and Frolov, I. (2002) Roles of nonstructural protein nsP2 and Alpha/Beta interferons in determining the outcome of Sindbis virus infection, J Virol. 76, 11254-11264.

21. Zhang, Y, Burke, C. W, Ryman, K. D., and Klimstra, W B. (2007) Identification and characterization of interferon-induced proteins that inhibit alphavirus replication, J Virol. 81, 11246-11255.

22. Schoggins, J. W. and Rice, C. M. (2011) Interferon-stimulated genes and their antiviral effector functions, Curr. Opin. Virol. 1, 519-525.

23. Simmons, J. D., White L J FAU—Morrison, T., Morrison T E FAU—Montgomery, S., Montgomery S A FAU—Whitmore, A., Whitmore A C FAU—Johnston, R., Johnston R E FAU—Heise, M., and Heise, M. T. Venezuelan equine encephalitis virus disrupts STAT1 signaling by distinct mechanisms independent of host shutoff.

24. Schoggins, J. W. (2014) Interferon-stimulated genes: roles in viral pathogenesis, Curr. Opin. Virol. 6, 40-46.

25. Hollidge, B. S., Weiss, S. R., and Soldan, S. S. (2011) The role of interferon antagonist, non-structural proteins in the pathogenesis and emergence of arboviruses, Viruses. 3, 629-658.

26. Akhrymuk, I., Kulemzin, S. V., and Frolova, E. I. (2012) Evasion of the innate immune response: the Old World alphavirus nsP2 protein induces rapid degradation of Rpb1, a catalytic subunit of RNA polymerase II, J Virol. 86, 7180-7191.

27. Garmashova, N., Gorchakov, R., Volkova, E., Paessler, S., Frolova, E., and Frolov, I. (2007) The Old World and New World alphaviruses use different virus-specific proteins for induction of transcriptional shutoff, J Virol. 81, 2472-2484.

28. Garmashova, N., Atasheva, S., Kang, W, Weaver, S. C., Frolova, E., and Frolov, I. (2007) Analysis of Venezuelan equine encephalitis virus capsid protein function in the inhibition of cellular transcription, J Virol. 81, 13552-13565.

29. Atasheva, S., Fish, A., Fornerod, M., and Frolova, E. I. (2010) Venezuelan equine Encephalitis virus capsid protein forms a tetrameric complex with CRM1 and importin alpha/beta that obstructs nuclear pore complex function, J Virol. 84, 4158-4171.

30. Hu, X., Compton, J. R., Leary, D. H., Olson, M. A., Lee, M. S., Cheung, J., Ye, W, Ferrer, M., Southall, N., Jadhav, A., Morazzani, E. M., Glass, P. J., Marugan, J., and Legler, P. M. (2016) Kinetic, Mutational, and Structural Studies of the Venezuelan Equine Encephalitis Virus Nonstructural Protein 2 Cysteine Protease, Biochemistry 55, 3007-3019.

31. Hirose, S., Nishizumi, H., and Sakano, H. (2003) Pub, a novel PU.1 binding protein, regulates the transcriptional activity of PU.1, Biochem Biophys Res. Commun. 311, 351-360.

32. Zhou, Z., Jia, X., Xue, Q., Dou, Z., Ma, Y, Zhao, Z., Jiang, Z., He, B., Jin, Q., and Wang, J. (2014) TRIM14 is a mitochondrial adaptor that facilitates retinoic acid-inducible gene-I-like receptor-mediated innate immune response, Proc. Natl. Acad. Sci. U.S.A 111, E245-E254.

33. Nenasheva, V. V., Kovaleva G V, F. A. U., Uryvaev L V, F. A. U., Ionova K S, F. A. U., dova A V, F. A. U., Vorkunova G K, F. A. U., Chernyshenko S V, F. A. U., Khaidarova N V, F. A. U., and Tarantul, V. Z. Enhanced expression of trim14 gene suppressed Sindbis virus reproduction and modulated the transcription of a large number of genes of innate immunity.

34. Balistreri, G., Caldentey, J., Kaariainen, L., and Ahola, T. (2007) Enzymatic defects of the nsP2 proteins of Semliki Forest virus temperature-sensitive mutants, J Virol. 81, 2849-2860.

35. Schechter, I. and Berger, A. (1967) On the size of the active site in proteases. I. Papain., Biochem. Biophys. Res. Commun. 27, 157-162.

36. Altschul, S. F., Gish, W, Miller, W, Myers, E. W, and Lipman, D. J. (1990) Basic local alignment search tool, J Mol. Biol. 215, 403410.

37. Strauss, E. G., De Groot, R. J., Levinson, R., and Strauss, J. H. (1992) Identification of the active site residues in the nsP2 proteinase of Sindbis virus, Virology 191, 932-940.

38. Uhlen, M., Fagerberg, L., Hallstrom, B. M., Lindskog, C., Oksvold, P., Mardinoglu, A., Sivertsson, A., Kampf, C., Sjostedt, E., Asplund, A., Olsson, I., Edlund, K., Lundberg, E., Navani, S., Szigyarto, C. A., Odeberg, J., Djureinovic, D., Takanen, J. O., Hober, S., Alm, T., Edqvist, P. H., Berling, H., Tegel, H., Mulder, J., Rockberg, J., Nilsson, P., Schwenk, J. M., Hamsten, M., von, F. K., Forsberg, M., Persson, L., Johansson, F., Zwahlen, M., von, H. G., Nielsen, J., and Ponten, F. (2015) Proteomics. Tissue-based map of the human proteome, Science 347, 1260419.

39. Jia, X., Zhou, H., Wu, C., Wu, Q., Ma, S., Wei, C., Cao, Y, Song, J., Zhong, H., Zhou, Z., and Wang, J. (2017) The Ubiquitin Ligase RNF125 Targets Innate Immune Adaptor Protein TRIM14 for Ubiquitination and Degradation, J Immunol 198, 4652-4658.

40. Wang, S., Chen, Y, Li, C., Wu, Y, Guo, L., Peng, C., Huang, Y., Cheng, G., and Qin, F. X. TRIM14 inhibits hepatitis C virus infection by SPRY domain-dependent targeted degradation of the viral NS5A protein.

41. Carthagena, L., Bergamaschi, A., Luna, J. M., David, A., Uchil, P. D., Margottin-Goguet, F., Mothes, W, Hazan, U., Transy, C., Pancino, G., and Nisole, S. A. (2009) Human TRIM Gene Expression in Response to Interferons, PLoS One 4, e4894.

42. Campos-Gomez, J., Ahmad, F., Rodriguez, E., and Saeed, M. F. (2016) A novel cell-based assay to measure activity of Venezuelan equine encephalitis virus nsP2 protease, Virology 496, 77-89.

43. D'Cruz, A. A., Babon, J. J., Norton, R. S., Nicola, N. A., and Nicholson, S. E. (2013) Structure and function of the SPRY/B30.2 domain proteins involved in innate immunity, Protein Sci 22, 1-10.

44. James, L. C., Keeble, A. H., Khan, Z., Rhodes, D. A., and Trowsdale, J. (2007) Structural basis for PRYSPRY-mediated tripartite motif (TRIM) protein function, Proc Natl Acad Sci USA 104, 6200-6205.

45. Ozato, K., Shin, D. M., Chang, T. H., and Morse, H. C., III (2008) TRIM family proteins and their emerging roles in innate immunity, Nat Rev Immunol 8, 849-860.

46. Vaysburd, M., Watkinson, R. E., Cooper, H., Reed, M., O'Connell, K., Smith, J., Cruickshanks, J., and James, L. C. (2013) Intracellular antibody receptor TRIM21 prevents fatal viral infection, Proc Natl Acad Sci USA 110, 12397-12401.

47. Di, P. A., Kajaste-Rudnitski, A., Oteiza, A., Nicora, L., Towers, G. J., Mechti, N., and Vicenzi, E. (2013) TRIM22 inhibits influenza A virus infection by targeting the viral nucleoprotein for degradation, J Virol. 87, 4523-4533.

48. Everett, R. D. and Chelbi-Alix, M. K. (2007) PML and PML nuclear bodies: implications in antiviral defence, Biochimie 89, 819-830.

49. Ozato, K., Shin, D. M., Chang, T. H., and Morse, H. C., III (2008) TRIM family proteins and their emerging roles in innate immunity, Nat Rev Immunol 8, 849-860.

50. James, L. C., Keeble, A. H., Khan, Z., Rhodes, D. A., and Trowsdale, J. (2007) Structural basis for PRYSPRY-mediated tripartite motif (TRIM) protein function, Proceedings of the National Academy of Sciences 104, 6200-6205.

51. Malim, M. H. and Bieniasz, P. D. (2012) HIV Restriction Factors and Mechanisms of Evasion, Cold Spring Harb. Perspect Med 2, a006940.

52. Nisole, S., Stoye, J. P., and Saib, A. (2005) TRIM family proteins: retroviral restriction and antiviral defence, Nat Rev Microbiol. 3, 799-808.

53. Carthagena, L., Bergamaschi, A., Luna, J. M., David, A., Uchil, P. D., Margottin-Goguet, F., Mothes, W, Hazan, U., Transy, C., Pancino, G., and Nisole, S. (2009) Human TRIM gene expression in response to interferons, PLoS One 4, e4894.

54. Bhoj, V. G., Sun, Q., Bhoj, E. J., Somers, C., Chen, X., Tones, J. P., Mejias, A., Gomez, A. M., Jafri, H., Ramilo, O., and Chen, Z. J. (2008) MAVS and MyD88 are essential for innate immunity but not cytotoxic T lymphocyte response against respiratory syncytial virus, Proc Natl Acad Sci USA 105, 14046-14051.

55. Mibayashi, M., Martinez-Sobrido, L. F., Loo Y M FAU—Cardenas, W, Cardenas W B FAU—Gale, M. J., Gale, M., Jr., and Garcia-Sastre, A. Inhibition of retinoic acid-inducible gene I-mediated induction of beta interferon by the NS1 protein of influenza A virus.

56. Kundu, P., Raychaudhuri, S., Tsai, W, and Dasgupta, A. (2005) Shutoff of RNA polymerase II transcription by poliovirus involves 3C protease-mediated cleavage of the TATA-binding protein at an alternative site: incomplete shutoff of transcription interferes with efficient viral replication, J Virol. 79, 9702-9713.

57. Das, S. and Dasgupta, A. (1993) Identification of the cleavage site and determinants required for poliovirus 3CPro-catalyzed cleavage of human TATA-binding transcription factor TBP, J Virol. 67, 3326-3331.

58. Weidman, M. K., Sharma, R., Raychaudhuri, S., Kundu, P., Tsai, W, and Dasgupta, A. (2003) The interaction of cytoplasmic RNA viruses with the nucleus, Virus Res. 95, 75-85.

59. Kuyumcu-Martinez, N. M., Van Eden, M. E., Younan, P., and Lloyd, R. E. (2004) Cleavage of poly(A)-binding protein by poliovirus 3C protease inhibits host cell translation: a novel mechanism for host translation shutoff, Mol Cell Biol 24, 1779-1790.

60. Kuyumcu-Martinez, N. M., Joachims, M., and Lloyd, R. E. (2002) Efficient cleavage of ribosome-associated poly (A)-binding protein by enterovirus 3C protease, J Virol. 76, 2062-2074.

61. de, B. S., Bonderoff, J. M., Chumakov, K. M., Lloyd, R. E., and Hellen, C. U. (2008) Cleavage of eukaryotic initiation factor eIF5B by enterovirus 3C proteases, Virology 378, 118-122.

62. Li, W, Ross-Smith, N., Proud, C. G., and Belsham, G. J. (2001) Cleavage of translation initiation factor 4AI (eIF4AI) but not eIF4AII by foot-and-mouth disease virus 3C protease: identification of the eIF4AI cleavage site, FEBS Lett 507, 1-5.

63. Foeger, N., Glaser, W, and Skern, T. (2002) Recognition of eukaryotic initiation factor 4G isoforms by picornaviral proteinases, J Biol Chem 277, 4430044309.

64. Qu, L., Feng, Z., Yamane, D., Liang, Y, Lanford, R. E., Li, K., and Lemon, S. M. (2011) Disruption of TLR3 signaling due to cleavage of TRIF by the hepatitis A virus protease-polymerase processing intermediate, 3CD, PLoS Pathog. 7, e1002169.

65. Banal, P. M., Sarkar, D., Fisher, P. B., and Racaniello, V. R. (2009) RIG-I is cleaved during picornavirus infection, Virology 391, 171-176.

66. Banal, P. M., Morrison, J. M., Drahos, J., Gupta, P., Sarkar, D., Fisher, P. B., and Racaniello, V. R. (2007) MDA-5 is cleaved in poliovirus-infected cells, J Virol. 81, 3677-3684.

67. Yang, Y., Liang, Y., Qu, L., Chen, Z., Yi, M., Li, K., and Lemon, S. M. (2007) Disruption of innate immunity due to mitochondrial targeting of a picornaviral protease precursor, Proc Natl Acad Sci USA 104, 7253-7258.

68. Neznanov, N., Chumakov, K. M., Neznanova, L., Almasan, A., Banerjee, A. K., and Gudkov, A. V. (2005) Proteolytic cleavage of the p65-RelA subunit of NF-kappaB during poliovirus infection, J Biol Chem 280, 24153-24158.

69. Wang, D., Fang, L., Li, K., Zhong, H., Fan, J., Ouyang, C., Zhang, H., Duan, E., Luo, R., Zhang, Z., Liu, X., Chen, H., and Xiao, S. (2012) Foot-and-mouth disease virus 3C protease cleaves NEMO to impair innate immune signaling, J Virol. 86, 9311-9322.

70. Wang, D., Fang, L., Wei, D., Zhang, H., Luo, R., Chen, H., Li, K., and Xiao, S. (2014) Hepatitis A virus 3C protease cleaves NEMO to impair induction of beta interferon, J Virol. 88, 10252-10258.

71. Lin, R., Lacoste, J., Nakhaei, P., Sun, Q., Yang, L., Paz, S., Wilkinson, P., Julkunen, I., Vitour, D., Meurs, E., and Hiscott, J. (2006) Dissociation of a MAVS/IPS-1/VISA/Cardif-IKKepsilon molecular complex from the mitochondrial outer membrane by hepatitis C virus NS3-4A proteolytic cleavage, J Virol. 80, 6072-6083.

72. Hiscott, J., Lacoste, J., and Lin, R. (2006) Recruitment of an interferon molecular signaling complex to the mitochondrial membrane: disruption by hepatitis C virus NS3-4A protease, Biochem. Pharmacol. 72, 1477-1484.

73. Bellecave, P., Sarasin-Filipowicz, M., Donze, O., Kennel, A., Gouttenoire, J., Meylan, E., Terracciano, L., Tschopp, J., Sarrazin, C., Berg, T., Moradpour, D., and Heim, M. H. (2010) Cleavage of mitochondrial antiviral signaling protein in the liver of patients with chronic hepatitis C correlates with a reduced activation of the endogenous interferon system, Hepatology 51, 1127-1136.

74. Meylan, E., Curran, J., Hofmann, K., Moradpour, D., Binder, M., Bartenschlager, R., and Tschopp, J. (2005) Cardif is an adaptor protein in the RIG-I antiviral pathway and is targeted by hepatitis C virus, Nature 437, 1167-1172.

75. Yu, C. Y, Chang, T. H., Liang, J. J., Chiang, R. L., Lee, Y L., Liao, C. L., and Lin, Y. L. (2012) Dengue Virus Targets the Adaptor Protein MITA to Subvert Host Innate Immunity, PLoS Pathog 8, e1002780.

76. Aguirre, S., Maestre, A. M., Pagni, S., Patel, J. R., Savage, T., Gutman, D., Maringer, K., Bernal-Rubio, D., Shabman, R. S., Simon, V., Rodriguez-Madoz, J. R., Mulder, L. C. F., Barber, G. N., and Fernandez-Sesma, A. (2012) DENV Inhibits Type I IFN Production in Infected Cells by Cleaving Human STING, PLoS Pathog 8, e1002934.

33

34

77. Li, J., Lim S P FAU—Beer, D., Beer, D. F., Patel, V. F., Wen, D. F., Tumanut, C. F., Tully D C FAU—Williams, J., Williams J A FAU—Jiricek, J., Jiricek, J. F., Priestle J P FAU—Harris, J., Harris J L FAU—Vasudevan, S., and Vasudevan, S. G. Functional profiling of recombinant NS3 proteases from all four serotypes of dengue virus using tetrapeptide and octapeptide substrate libraries.

78. Blom, N., Hansen, J., Blaas, D., and Brunak, S. (1996) Cleavage site analysis in picornaviral polyproteins: discovering cellular targets by neural networks, Protein Sci 5, 2203-2216.

79. Mukherjee, A., Morosky, S. A., orme-Axford, E., Dybdahl-Sissoko, N., Oberste, M. S., Wang, T., and Coyne, C. B. (2011) The coxsackievirus B 3C protease cleaves MAVS and TRIF to attenuate host type I interferon and apoptotic signaling, PLoS Pathog. 7, e1001311.

80. Badorff, C., Berkely, N., Mehrotra, S., Talhouk, J. W, Rhoads, R. E., and Knowlton, K. U. (2000) Enteroviral protease 2A directly cleaves dystrophin and is inhibited by a dystrophin-based substrate analogue, J Biol Chem 275, 11191-11197.

81. Weidman, M. K., Sharma, R., Raychaudhuri, S., Kundu, P., Tsai, W, and Dasgupta, A. (2003) The interaction of cytoplasmic RNA viruses with the nucleus, Virus Res. 95, 75-85.

82. Falk, M. M., Grigera, P. R., Bergmann, I. E., Zibert, A., Multhaup, G., and Beck, E. (1990) Foot-and-mouth disease virus protease 3C induces specific proteolytic cleavage of host cell histone H3, J Virol 64, 748-756.

83. Yalamanchili, P., Banerjee, R., and Dasgupta, A. (1997) Poliovirus-encoded protease 2APro cleaves the TATA-binding protein but does not inhibit host cell RNA polymerase II transcription in vitro, J Virol 71, 6881-6886.

84. Donnelly, M. I., Zhou, M., Millard, C. S., Clancy, S., Stols, L., Eschenfeldt, W H., Collart, F. R., and Joachimiak, A. (2006) An expression vector tailored for large-scale, high-throughput purification of recombinant proteins, Protein Expr. Purif. 47, 446454.

85. Legler, P. M., Cai, M., Peterkofsky, A., and Clore, G. M. (2004) Three-dimensional solution structure of the cytoplasmic B domain of the mannitol transporter IImannitol of the *Escherichia coli* phosphotransferase system, J. Biol. Chem. 279, 39115-39121.

86. Cheung, J., Franklin, M., Mancia, F., Rudolph, M., Cassidy, M., Gary, E., Burshteyn, F., and Love, J. (2011) Structure of the Chikungunya virus nsP2 protease.

87. Dong, M., Tepp, W. H., Johnson, E. A., and Chapman, E. R. (2004) Using fluorescent sensors to detect botulinum neurotoxin activity in vitro and in living cells, Proc. Natl. Acad. Sci. U.S.A 101, 14701-14706.

88. Ruge, D. R., Dunning, F. M., Piazza, T. M., Molles, B. E., Adler, M., Zeytin, F. N., and Tucker, W. C. (2011) Detection of six serotypes of botulinum neurotoxin using fluorogenic reporters, Anal. Biochem. 411, 200-209.

89. Morris, G. M., Huey, R., Lindstrom, W, Sanner, M. F., Belew, R. K., Goodsell, D. S., and Olson, A. J. (2009) AutoDock4 and AutoDockTools4: Automated docking with selective receptor flexibility, J Comput. Chem. 30, 2785-2791.

90. Shin, G., Yost, S. A., Miller, M. T., Elrod, E. J., Grakoui, A., and Marcotrigiano, J. (2012) Structural and functional insights into alphavirus polyprotein processing and pathogenesis, Proc. Natl. Acad. Sci. U.S.A 109, 16534-16539.

91. James, L. C., Keeble, A. H., Khan, Z., Rhodes, D. A., and Trowsdale, J. (2007) Structural basis for PRYSPRY-mediated tripartite motif (TRIM) protein function, Proceedings of the National Academy of Sciences 104, 6200-6205.

92. (2017) Introduction to CRISPR and Cas9.

93. Hartig, J. S. (2017) Mechanism of siRNA silencing.

94. Morazzani E M, Compton J R, Leary D H, Berry A V, Hu X, Marugan J J, Glass P J, Legler P M. Proteolytic cleavage of host proteins by the Group IV viral proteases of Venezuelan equine encephalitis virus and Zika virus. Antiviral Res. 2019 April; 164:106-122. doi: 10.1016/j.antiviral.2019.02.001

95. Nathanael D. Reynolds, Nathalie M. Aceves, Jinny L. Liu, Jaimee R. Compton, Dagmar H. Leary, Brendan T. Freitas, Scott D. Pegan, Katarina Z. Doctor, Fred Y. Wu, Xin Hu, and Patricia M. Legler, "The SARS-CoV-2 SSHHPS Recognized by the Papain-like Protease" *ACS Infect. Dis.* 2021, 7, 6, 1483-1502, published May 21, 2021

96. Stabell A C, Meyerson N R, Gullberg R C, Gilchrist A R, Webb K J, Old W M, Perera R, Sawyer S L. Dengue viruses cleave STING in humans but not in nonhuman primates, their presumed natural reservoir. Elife. 2018 Mar. 20; 7:e31919. doi: 10.7554/eLife.31919. PMID: 29557779; PMCID: PMC5860865.

97. Badorff C, Knowlton K U. Dystrophin disruption in enterovirus-induced myocarditis and dilated cardiomyopathy: from bench to bedside. Med Microbiol Immunol. 2004 May; 193(2-3):121-6. doi: 10.1007/s00430-003-0189-7. Epub 2003 Aug. 12. PMID: 12920582.

98. Lim B K, Peter A K, Xiong D, Narezkina A, Yung A, Dalton N D, Hwang K K, Yajima T, Chen J, Knowlton K U. Inhibition of Coxsackievirus-associated dystrophin cleavage prevents cardiomyopathy. J Clin Invest. 2013 December; 123(12):5146-51. doi: 10.1172/JCI66271. Epub 2013 Nov. 8. PMID: 24200690; PMCID: PMC3859391.

99. Perez-Bermejo J A, Kang S, Rockwood S J, Simoneau C R, Joy D A, Silva A C, Ramadoss G N, Flanigan W R, Fozouni P, Li H, Chen P Y, Nakamura K, Whitman J D, Hanson P J, McManus B M, Ott M, Conklin B R, McDevitt T C. SARS-CoV-2 infection of human iPSC-derived cardiac cells reflects cytopathic features in hearts of patients with COVID-19. Sci Transl Med. 2021 Apr. 21; 13(590):eabf7872. doi: 10.1126/scitranslmed.abf7872. Epub 2021 Mar. 15. PMID: 33723017; PMCID: PMC8128284.

100. Perez-Bermejo et al., "SARS-CoV-2 infection of human iPSC-derived cardiac cells reflects cytopathic features in hearts of patients with COVID-19" Sci. Transl. Med. 13, eabf7872 (2021) 21 Apr. 2021.

101. Li H, Saucedo-Cuevas L, Yuan L, et al. "Zika Virus Protease Cleavage of Host Protein Septin-2 Mediates Mitotic Defects in Neural Progenitors." Neuron. 2019; 101(6):1089-1098.e4. doi:10.1016/j.neuron.2019.01.010.

---

What is claimed is:

1. A method of post-translational silencing and transient loss of function of a target protein, consisting of:
   expressing a viral protease of a Venezuelan equine encephalitis virus (VEEV) in a mammalian host cell within a living organism by infecting the organism via administering an attenuated VEEV virus encoding the viral protease,
   wherein the viral protease recognizes and cleaves a target protein sequence endogenous to the host, thereby causing transient loss of function of a target protein that comprises the target protein sequence, and
   halting protease activity by introducing a protease inhibitor to the host cell.

2. The method of claim 1, wherein the viral protease comprises VEEV nsP2 protease, and the target protein comprises human TRIM14 protein, such that the nsP2 protease cleaves the human TRIM14 protein.

* * * * *

SEQUENCE LISTING

<160> NUMBER OF SEQ ID NOS: 29

<210> SEQ ID NO 1

```
<211> LENGTH: 6
<212> TYPE: PRT
<213> ORGANISM: Artificial Sequence
<220> FEATURE:
<223> OTHER INFORMATION: synthetic construct

<400> SEQUENCE: 1

Gln Glu Ala Gly Ala Gly
1               5

<210> SEQ ID NO 2
<211> LENGTH: 25
<212> TYPE: PRT
<213> ORGANISM: Artificial Sequence
<220> FEATURE:
<223> OTHER INFORMATION: synthetic construct

<400> SEQUENCE: 2

Val Glu Glu Pro Thr Leu Glu Ala Asp Val Asp Leu Met Leu Gln Glu
1               5                   10                  15

Ala Gly Ala Gly Ser Val Glu Thr Pro
            20                  25

<210> SEQ ID NO 3
<211> LENGTH: 25
<212> TYPE: PRT
<213> ORGANISM: Artificial Sequence
<220> FEATURE:
<223> OTHER INFORMATION: synthetic construct

<400> SEQUENCE: 3

Thr Arg Glu Glu Phe Glu Ala Phe Val Ala Gln Gln Gln Arg Phe Asp
1               5                   10                  15

Ala Gly Ala Tyr Ile Phe Ser Ser Asp
            20                  25

<210> SEQ ID NO 4
<211> LENGTH: 25
<212> TYPE: PRT
<213> ORGANISM: Artificial Sequence
<220> FEATURE:
<223> OTHER INFORMATION: synthetic construct

<400> SEQUENCE: 4

Asp Cys Phe Ala Thr Gly Arg His Tyr Trp Glu Val Asp Val Gln Glu
1               5                   10                  15

Ala Gly Ala Gly Trp Trp Val Gly Ala
            20                  25

<210> SEQ ID NO 5
<211> LENGTH: 22
<212> TYPE: PRT
<213> ORGANISM: Artificial Sequence
<220> FEATURE:
<223> OTHER INFORMATION: synthetic construct

<400> SEQUENCE: 5

Ala Thr Gly Arg His Tyr Trp Glu Val Asp Val Gln Glu Ala Gly Ala
1               5                   10                  15

Gly Trp Trp Val Gly Ala
            20

<210> SEQ ID NO 6
<211> LENGTH: 19
<212> TYPE: PRT
```

-continued

```
<213> ORGANISM: Artificial Sequence
<220> FEATURE:
<223> OTHER INFORMATION: synthetic construct

<400> SEQUENCE: 6

Arg His Tyr Trp Glu Val Asp Val Gln Glu Ala Gly Ala Gly Trp Trp
1               5                   10                  15

Val Gly Ala

<210> SEQ ID NO 7
<211> LENGTH: 16
<212> TYPE: PRT
<213> ORGANISM: Artificial Sequence
<220> FEATURE:
<223> OTHER INFORMATION: synthetic construct

<400> SEQUENCE: 7

Glu Ala Glu Gln Ile Ala Leu Lys Gly Gly Lys Lys Gln Leu Gln Lys
1               5                   10                  15

<210> SEQ ID NO 8
<211> LENGTH: 23
<212> TYPE: PRT
<213> ORGANISM: Artificial Sequence
<220> FEATURE:
<223> OTHER INFORMATION: synthetic construct

<400> SEQUENCE: 8

Gly Gly Pro His Arg Leu Asp Glu Ala Glu Gln Ile Ala Leu Lys Gly
1               5                   10                  15

Gly Lys Lys Gln Leu Gln Lys
            20

<210> SEQ ID NO 9
<211> LENGTH: 20
<212> TYPE: PRT
<213> ORGANISM: Artificial Sequence
<220> FEATURE:
<223> OTHER INFORMATION: synthetic construct

<400> SEQUENCE: 9

Ile Tyr His Ser Ala Trp Leu Leu Ile Ala Leu Arg Gly Gly Lys Ile
1               5                   10                  15

Glu Val Gln Leu
            20

<210> SEQ ID NO 10
<211> LENGTH: 16
<212> TYPE: PRT
<213> ORGANISM: Artificial Sequence
<220> FEATURE:
<223> OTHER INFORMATION: synthetic construct

<400> SEQUENCE: 10

Leu Lys Asn Leu Thr Glu Ile Leu Asn Gly Gly Val Tyr Val Asp Gln
1               5                   10                  15

<210> SEQ ID NO 11
<211> LENGTH: 18
<212> TYPE: PRT
<213> ORGANISM: Artificial Sequence
<220> FEATURE:
<223> OTHER INFORMATION: synthetic construct

<400> SEQUENCE: 11
```

-continued

Gly Gly Thr Phe Gln Gly Arg Asp Leu Arg Gly Gly Ala His Ala Ser
1               5                   10                  15

Ser Ser

<210> SEQ ID NO 12
<211> LENGTH: 25
<212> TYPE: PRT
<213> ORGANISM: Artificial Sequence
<220> FEATURE:
<223> OTHER INFORMATION: synthetic construct

<400> SEQUENCE: 12

Leu Leu Gly Ala Arg Gly Pro Gly Gly Thr Phe Gln Gly Arg Asp Leu
1               5                   10                  15

Arg Gly Gly Ala His Ala Ser Ser Ser
            20                  25

<210> SEQ ID NO 13
<211> LENGTH: 19
<212> TYPE: PRT
<213> ORGANISM: Artificial Sequence
<220> FEATURE:
<223> OTHER INFORMATION: synthetic construct

<400> SEQUENCE: 13

Arg His Tyr Trp Glu Val Asp Val Gln Glu Ala Gly Ala Gly Trp Trp
1               5                   10                  15

Val Gly Ala

<210> SEQ ID NO 14
<211> LENGTH: 22
<212> TYPE: PRT
<213> ORGANISM: Artificial Sequence
<220> FEATURE:
<223> OTHER INFORMATION: synthetic construct

<400> SEQUENCE: 14

Ala Thr Gly Arg His Tyr Trp Glu Val Asp Val Gln Glu Ala Gly Ala
1               5                   10                  15

Gly Trp Trp Val Gly Ala
            20

<210> SEQ ID NO 15
<211> LENGTH: 25
<212> TYPE: PRT
<213> ORGANISM: Artificial Sequence
<220> FEATURE:
<223> OTHER INFORMATION: synthetic construct

<400> SEQUENCE: 15

Asp Cys Phe Ala Thr Gly Arg His Tyr Trp Glu Val Asp Val Gln Glu
1               5                   10                  15

Ala Gly Ala Gly Trp Trp Val Gly Ala
            20                  25

<210> SEQ ID NO 16
<211> LENGTH: 17
<212> TYPE: PRT
<213> ORGANISM: Artificial Sequence
<220> FEATURE:
<223> OTHER INFORMATION: synthetic construct

<400> SEQUENCE: 16

Asp Val Glu Glu Leu Glu Tyr His Ala Gly Ala Gly Val Val Glu Thr

-continued

```
1               5                10               15

Pro

<210> SEQ ID NO 17
<211> LENGTH: 25
<212> TYPE: PRT
<213> ORGANISM: Artificial Sequence
<220> FEATURE:
<223> OTHER INFORMATION: synthetic construct

<400> SEQUENCE: 17

Ala Glu Thr Gly Val Val Asp Val Asp Val Glu Glu Leu Glu Tyr His
1               5                10               15

Ala Gly Ala Gly Val Val Glu Thr Pro
            20               25

<210> SEQ ID NO 18
<211> LENGTH: 25
<212> TYPE: PRT
<213> ORGANISM: Artificial Sequence
<220> FEATURE:
<223> OTHER INFORMATION: synthetic construct

<400> SEQUENCE: 18

Leu Ser Ser Thr Leu Thr Asn Ile Tyr Thr Gly Ser Arg Leu His Glu
1               5                10               15

Ala Gly Cys Ala Pro Ser Tyr His Val
            20               25

<210> SEQ ID NO 19
<211> LENGTH: 25
<212> TYPE: PRT
<213> ORGANISM: Artificial Sequence
<220> FEATURE:
<223> OTHER INFORMATION: synthetic construct

<400> SEQUENCE: 19

Met Gly Ile Gly Arg Ser Glu Gly Gly Arg Arg Gly Ala Ala Leu Gly
1               5                10               15

Val Leu Leu Ala Leu Gly Ala Ala Leu
            20               25

<210> SEQ ID NO 20
<211> LENGTH: 35
<212> TYPE: PRT
<213> ORGANISM: Artificial Sequence
<220> FEATURE:
<223> OTHER INFORMATION: synthetic construct

<400> SEQUENCE: 20

Pro Val Arg Ser Ser Ala Pro Arg Arg Gly His Ser Val Ala Ser Ala
1               5                10               15

Pro Arg Ser Gly Leu Arg Gln Val Ala Gly Arg Arg Gly Ala Ala Leu
            20               25               30

Pro Cys Ser
        35

<210> SEQ ID NO 21
<211> LENGTH: 34
<212> TYPE: PRT
<213> ORGANISM: Artificial Sequence
<220> FEATURE:
<223> OTHER INFORMATION: synthetic construct
```

-continued

<400> SEQUENCE: 21

Met Ile Arg Leu Gly Gly Trp Cys Ala Arg Arg Leu Cys Ser Ala Ala
1               5                   10                  15

Val Pro Ala Gly Arg Arg Gly Ala Ala Gly Gly Leu Gly Leu Ala Gly
            20                  25                  30

Gly Arg

<210> SEQ ID NO 22
<211> LENGTH: 21
<212> TYPE: PRT
<213> ORGANISM: Artificial Sequence
<220> FEATURE:
<223> OTHER INFORMATION: synthetic construct

<400> SEQUENCE: 22

Arg Ser Thr Thr Ser Arg Ala Lys Leu Ala Phe Lys Arg Gly Ala Arg
1               5                   10                  15

Leu Thr Ser Thr Gly
            20

<210> SEQ ID NO 23
<211> LENGTH: 34
<212> TYPE: PRT
<213> ORGANISM: Artificial Sequence
<220> FEATURE:
<223> OTHER INFORMATION: synthetic construct

<400> SEQUENCE: 23

Met Leu Gln Gly Pro Gly Ser Leu Leu Leu Leu Phe Leu Ala Ser His
1               5                   10                  15

Cys Cys Leu Gly Ser Ala Arg Gly Leu Phe Leu Phe Gly Gln Pro Asp
            20                  25                  30

Phe Ser

<210> SEQ ID NO 24
<211> LENGTH: 34
<212> TYPE: PRT
<213> ORGANISM: Artificial Sequence
<220> FEATURE:
<223> OTHER INFORMATION: synthetic construct

<400> SEQUENCE: 24

Met Phe Leu Ser Ile Leu Val Ala Leu Cys Leu Trp Leu His Leu Ala
1               5                   10                  15

Leu Gly Val Arg Gly Ala Pro Cys Glu Ala Val Arg Ile Pro Met Cys
            20                  25                  30

Arg His

<210> SEQ ID NO 25
<211> LENGTH: 467
<212> TYPE: PRT
<213> ORGANISM: Artificial Sequence
<220> FEATURE:
<223> OTHER INFORMATION: synthetic construct

<400> SEQUENCE: 25

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp

-continued

```
         35                40                45

Glu Tyr Gln Gly Lys Leu Thr Val Ala Lys Leu Asn Ile Asp Gln Asn
    50                55                60

Pro Gly Thr Ala Pro Lys Tyr Gly Ile Arg Gly Ile Pro Thr Leu Leu
65                70                75                80

Leu Phe Lys Asn Gly Glu Val Ala Ala Thr Lys Val Gly Ala Leu Ser
                85                90                95

Lys Gly Gln Leu Lys Glu Phe Leu Asp Ala Asn Leu Ala Gly Ser Gly
            100               105               110

Ser Gly His Met His His His His His His Ser Ser Gly Leu Val Pro
            115               120               125

Arg Gly Ser Met Arg His Ile Leu Glu Arg Pro Asp Pro Thr Asp Val
    130               135               140

Phe Gln Asn Lys Ala Asn Val Cys Trp Ala Lys Ala Leu Val Pro Val
145               150               155               160

Leu Lys Thr Ala Gly Ile Asp Met Thr Thr Glu Gln Trp Asn Thr Val
                165               170               175

Asp Tyr Phe Glu Thr Asp Lys Ala His Ser Ala Glu Ile Val Leu Asn
            180               185               190

Gln Leu Cys Val Arg Phe Phe Gly Leu Asp Leu Asp Ser Gly Leu Phe
            195               200               205

Ser Ala Pro Thr Val Pro Leu Ser Ile Arg Asn Asn His Trp Asp Asn
    210               215               220

Ser Pro Ser Pro Asn Met Tyr Gly Leu Asn Lys Glu Val Val Arg Gln
225               230               235               240

Leu Ser Arg Arg Tyr Pro Gln Leu Pro Arg Ala Val Ala Thr Gly Arg
                245               250               255

Val Tyr Asp Met Asn Thr Gly Thr Leu Arg Asn Tyr Asp Pro Arg Ile
            260               265               270

Asn Leu Val Pro Val Asn Arg Arg Leu Pro His Ala Leu Val Leu His
            275               280               285

His Asn Glu His Pro Gln Ser Asp Phe Ser Ser Phe Val Ser Lys Leu
    290               295               300

Lys Gly Arg Thr Val Leu Val Val Gly Glu Lys Leu Ser Val Pro Gly
305               310               315               320

Lys Met Val Asp Trp Leu Ser Asp Arg Pro Glu Ala Thr Phe Arg Ala
                325               330               335

Arg Leu Asp Leu Gly Ile Pro Gly Asp Val Pro Lys Tyr Asp Ile Ile
            340               345               350

Phe Val Asn Val Arg Thr Pro Tyr Lys Tyr His His Tyr Gln Gln Cys
            355               360               365

Glu Asp His Ala Ile Lys Leu Ser Met Leu Thr Lys Lys Ala Cys Leu
    370               375               380

His Leu Asn Pro Gly Gly Thr Cys Val Ser Ile Gly Tyr Gly Tyr Ala
385               390               395               400

Asp Arg Ala Ser Glu Ser Ile Ile Gly Ala Ile Ala Arg Gln Phe Lys
                405               410               415

Phe Ser Arg Val Cys Lys Pro Lys Ser Ser Leu Glu Glu Thr Glu Val
            420               425               430

Leu Phe Val Phe Ile Gly Tyr Asp Arg Lys Ala Arg Thr His Asn Pro
            435               440               445

Tyr Lys Leu Ser Ser Thr Leu Thr Asn Ile Tyr Thr Gly Ser Arg Leu
    450               455               460
```

His Glu Ala
465

<210> SEQ ID NO 26
<211> LENGTH: 336
<212> TYPE: PRT
<213> ORGANISM: Artificial Sequence
<220> FEATURE:
<223> OTHER INFORMATION: synthetic construct

<400> SEQUENCE: 26

Met Gly Ser Ser His His His His His His Ser Ser Gly Leu Val Pro
1               5                   10                  15

Arg Gly Ser His Met Glu Val Arg Thr Ile Lys Val Phe Thr Thr Val
            20                  25                  30

Asp Asn Ile Asn Leu His Thr Gln Val Val Asp Met Ser Met Thr Tyr
        35                  40                  45

Gly Gln Gln Phe Gly Pro Thr Tyr Leu Asp Gly Ala Asp Val Thr Lys
    50                  55                  60

Ile Lys Pro His Asn Ser His Glu Gly Lys Thr Phe Tyr Val Leu Pro
65                  70                  75                  80

Asn Asp Asp Thr Leu Arg Val Glu Ala Phe Glu Tyr Tyr His Thr Thr
                85                  90                  95

Asp Pro Ser Phe Leu Gly Arg Tyr Met Ser Ala Leu Asn His Thr Lys
            100                 105                 110

Lys Trp Lys Tyr Pro Gln Val Asn Gly Leu Thr Ser Ile Lys Trp Ala
            115                 120                 125

Asp Asn Asn Cys Tyr Leu Ala Thr Ala Leu Leu Thr Leu Gln Gln Ile
        130                 135                 140

Glu Leu Lys Phe Asn Pro Pro Ala Leu Gln Asp Ala Tyr Tyr Arg Ala
145                 150                 155                 160

Arg Ala Gly Glu Ala Ala Asn Phe Cys Ala Leu Ile Leu Ala Tyr Cys
                165                 170                 175

Asn Lys Thr Val Gly Glu Leu Gly Asp Val Arg Glu Thr Met Ser Tyr
            180                 185                 190

Leu Phe Gln His Ala Asn Leu Asp Ser Cys Lys Arg Val Leu Asn Val
            195                 200                 205

Val Cys Lys Thr Cys Gly Gln Gln Gln Thr Thr Leu Lys Gly Val Glu
        210                 215                 220

Ala Val Met Tyr Met Gly Thr Leu Ser Tyr Glu Gln Phe Lys Lys Gly
225                 230                 235                 240

Val Gln Ile Pro Cys Thr Cys Gly Lys Gln Ala Thr Lys Tyr Leu Val
                245                 250                 255

Gln Gln Glu Ser Pro Phe Val Met Met Ser Ala Pro Pro Ala Gln Tyr
            260                 265                 270

Glu Leu Lys His Gly Thr Phe Thr Cys Ala Ser Glu Tyr Thr Gly Asn
            275                 280                 285

Tyr Gln Cys Gly His Tyr Lys His Ile Thr Ser Lys Glu Thr Leu Tyr
        290                 295                 300

Cys Ile Asp Gly Ala Leu Leu Thr Lys Ser Ser Glu Tyr Lys Gly Pro
305                 310                 315                 320

Ile Thr Asp Val Phe Tyr Lys Glu Asn Ser Tyr Thr Thr Thr Ile Lys
                325                 330                 335

<210> SEQ ID NO 27

```
<211> LENGTH: 361
<212> TYPE: PRT
<213> ORGANISM: Artificial Sequence
<220> FEATURE:
<223> OTHER INFORMATION: synthetic construct

<400> SEQUENCE: 27

Met Gly Ser Ser His His His His His His Ser Ser Gly Leu Val Pro
1               5                   10                  15

Arg Gly Ser His Met Gly Ser Ser His His His His His Ser Ser
            20                  25                  30

Gly Leu Val Pro Arg Gly Ser Gln Leu Thr Ile Glu Val Leu Val Thr
            35                  40                  45

Val Asp Gly Val Asn Phe Arg Thr Val Val Leu Asn Asn Lys Asn Thr
        50                  55                  60

Tyr Arg Ser Gln Leu Gly Cys Val Phe Phe Asn Gly Ala Asp Ile Ser
65                  70                  75                  80

Asp Thr Ile Pro Asp Glu Lys Gln Asn Gly His Ser Leu Tyr Leu Ala
                85                  90                  95

Asp Asn Leu Thr Ala Asp Glu Thr Lys Ala Leu Lys Glu Leu Tyr Gly
            100                 105                 110

Pro Val Asp Pro Thr Phe Leu His Arg Phe Tyr Ser Leu Lys Ala Ala
            115                 120                 125

Val His Gly Trp Lys Met Val Val Cys Asp Lys Val Arg Ser Leu Lys
        130                 135                 140

Leu Ser Asp Asn Asn Cys Tyr Leu Asn Ala Val Ile Met Thr Leu Asp
145                 150                 155                 160

Leu Leu Lys Asp Ile Lys Phe Val Ile Pro Ala Leu Gln His Ala Phe
                165                 170                 175

Met Lys His Lys Gly Gly Asp Ser Thr Asp Phe Ile Ala Leu Ile Met
            180                 185                 190

Ala Tyr Gly Asn Cys Thr Phe Gly Ala Pro Asp Asp Ala Ser Arg Leu
            195                 200                 205

Leu His Thr Val Leu Ala Lys Ala Glu Leu Cys Cys Ser Ala Arg Met
        210                 215                 220

Val Trp Arg Glu Trp Cys Asn Val Cys Gly Ile Lys Asp Val Val Leu
225                 230                 235                 240

Gln Gly Leu Lys Ala Cys Cys Tyr Val Gly Val Gln Thr Val Glu Asp
            245                 250                 255

Leu Arg Ala Arg Met Thr Tyr Val Cys Gln Cys Gly Gly Glu Arg His
            260                 265                 270

Arg Gln Leu Val Glu His Thr Thr Pro Trp Leu Leu Leu Ser Gly Thr
        275                 280                 285

Pro Asn Glu Lys Leu Val Thr Thr Ser Thr Ala Pro Asp Phe Val Ala
    290                 295                 300

Phe Asn Val Phe Gln Gly Ile Glu Thr Ala Val Gly His Tyr Val His
305                 310                 315                 320

Ala Arg Leu Lys Gly Gly Leu Ile Leu Lys Phe Asp Ser Gly Thr Val
            325                 330                 335

Ser Lys Thr Ser Asp Trp Lys Cys Lys Val Thr Asp Val Leu Phe Pro
            340                 345                 350

Gly Gln Lys Tyr Ser Ser Asp Cys Asn
        355                 360

<210> SEQ ID NO 28
```

-continued

```
<211> LENGTH: 247
<212> TYPE: PRT
<213> ORGANISM: Artificial Sequence
<220> FEATURE:
<223> OTHER INFORMATION: synthetic construct

<400> SEQUENCE: 28

Met Gly Ser Ser His His His His His His Ser Ser Gly Leu Val Pro
1               5                   10                  15

Arg Gly Ser His Met Val Asp Met Tyr Ile Glu Arg Ala Gly Asp Ile
            20                  25                  30

Thr Trp Glu Lys Asp Ala Glu Val Thr Gly Asn Ser Pro Arg Leu Asp
            35                  40                  45

Val Ala Leu Asp Glu Ser Gly Asp Phe Ser Leu Val Glu Asp Asp Gly
        50                  55                  60

Pro Pro Met Ala Gly Gly Gly Gly Ser Gly Gly Gly Ser Gly Ala
65                  70                  75                  80

Leu Trp Asp Val Pro Ala Pro Lys Glu Val Lys Lys Gly Glu Thr Thr
                85                  90                  95

Asp Gly Val Tyr Arg Val Met Thr Arg Gly Leu Leu Gly Ser Thr Gln
            100                 105                 110

Val Gly Val Gly Val Met Gln Glu Gly Val Phe His Thr Met Trp His
        115                 120                 125

Val Thr Lys Gly Ser Ala Leu Arg Ser Gly Glu Gly Arg Leu Asp Pro
    130                 135                 140

Tyr Trp Gly Asp Val Lys Gln Asp Leu Val Ser Tyr Ser Gly Pro Trp
145                 150                 155                 160

Lys Leu Asp Ala Ala Trp Asp Gly His Ser Glu Val Gln Leu Leu Ala
                165                 170                 175

Val Pro Pro Gly Glu Arg Ala Arg Asn Ile Gln Thr Leu Pro Gly Ile
            180                 185                 190

Phe Lys Thr Lys Asp Gly Asp Ile Gly Ala Val Ala Leu Asp Tyr Pro
            195                 200                 205

Ala Gly Thr Ser Gly Ser Pro Ile Leu Asp Lys Ser Gly Arg Val Ile
    210                 215                 220

Gly Leu Tyr Gly Asn Gly Val Val Ile Lys Asn Gly Ser Tyr Val Ser
225                 230                 235                 240

Ala Ile Thr Gln Gly Arg Arg
                245

<210> SEQ ID NO 29
<211> LENGTH: 324
<212> TYPE: PRT
<213> ORGANISM: Artificial Sequence
<220> FEATURE:
<223> OTHER INFORMATION: synthetic construct

<400> SEQUENCE: 29

Ser Asn Ala Phe Gln Asn Lys Ala Asn Val Cys Trp Ala Lys Ser Leu
1               5                   10                  15

Val Pro Ile Leu Glu Thr Ala Gly Ile Lys Leu Asn Asp Arg Gln Trp
            20                  25                  30

Ser Gln Ile Ile Gln Ala Phe Lys Glu Asp Lys Ala Tyr Ser Pro Glu
            35                  40                  45

Val Ala Leu Asn Glu Ile Cys Thr Arg Met Tyr Gly Val Asp Leu Asp
        50                  55                  60

Ser Gly Leu Phe Ser Lys Pro Leu Val Ser Val Tyr Tyr Ala Asp Asn
```

-continued

```
65                  70                  75                  80

His Trp Asp Asn Arg Pro Gly Gly Lys Met Phe Gly Phe Asn Pro Glu
                85                  90                  95

Ala Ala Ser Ile Leu Glu Arg Lys Tyr Pro Phe Thr Lys Gly Lys Trp
            100                 105                 110

Asn Ile Asn Lys Gln Ile Cys Val Thr Thr Arg Arg Ile Glu Asp Phe
        115                 120                 125

Asn Pro Thr Thr Asn Ile Ile Pro Val Asn Arg Arg Leu Pro His Ser
    130                 135                 140

Leu Val Ala Glu His Arg Pro Val Lys Gly Glu Arg Met Glu Trp Leu
145                 150                 155                 160

Val Asn Lys Ile Asn Gly His His Val Leu Leu Val Ser Gly Tyr Asn
            165                 170                 175

Leu Ala Leu Pro Thr Lys Arg Val Thr Trp Val Ala Pro Leu Gly Val
            180                 185                 190

Arg Gly Ala Asp Tyr Thr Tyr Asn Leu Glu Leu Gly Leu Pro Ala Thr
            195                 200                 205

Leu Gly Arg Tyr Asp Leu Val Val Ile Asn Ile His Thr Pro Phe Arg
    210                 215                 220

Ile His His Tyr Gln Gln Cys Val Asp His Ala Met Lys Leu Gln Met
225                 230                 235                 240

Leu Gly Gly Asp Ser Leu Arg Leu Leu Lys Pro Gly Gly Ser Leu Leu
            245                 250                 255

Ile Arg Ala Tyr Gly Tyr Ala Asp Arg Thr Ser Glu Arg Val Ile Cys
            260                 265                 270

Val Leu Gly Arg Lys Phe Arg Ser Ser Arg Ala Leu Lys Pro Pro Cys
    275                 280                 285

Val Thr Ser Asn Thr Glu Met Phe Phe Leu Phe Ser Asn Phe Asp Asn
    290                 295                 300

Gly Arg Arg Asn Phe Thr Thr His Val Met Asn Asn Gln Leu Asn Ala
305                 310                 315                 320

Ala Phe Val Gly
```